United States Patent
Songer

(10) Patent No.: US 10,376,379 B2
(45) Date of Patent: Aug. 13, 2019

(54) BONE STABILIZATION IMPLANTS, INSTRUMENTS, AND METHODS

(71) Applicant: Zavation Medical Products, LLC, Flowood, MS (US)

(72) Inventor: Matthew Songer, Marquette, MI (US)

(73) Assignee: Zavation Medical Products, LLC, Flowood, MS (US)

(*) Notice: Subject to any disclaimer, the term of this patent is extended or adjusted under 35 U.S.C. 154(b) by 0 days.

(21) Appl. No.: 15/343,191

(22) Filed: Nov. 3, 2016

(65) Prior Publication Data
US 2017/0065427 A1  Mar. 9, 2017

Related U.S. Application Data

(63) Continuation-in-part of application No. 14/453,520, filed on Aug. 6, 2014, now Pat. No. 9,592,131, and a
(Continued)

(51) Int. Cl.
*A61B 17/17* (2006.01)
*A61B 17/70* (2006.01)
(Continued)

(52) U.S. Cl.
CPC ........ *A61F 2/4455* (2013.01); *A61B 17/7076* (2013.01); *A61F 2/4611* (2013.01);
(Continued)

(58) Field of Classification Search
CPC .... A61F 2/4455; A61F 2/4611; A61F 2/4465;
A61F 2002/2835; A61F 2002/30133;
A61F 2002/30135; A61F 2002/30136;
A61F 2002/30164; A61F 2002/30166;
A61F 2002/30172; A61F 2002/30182;
A61F 2002/30197; A61F 2002/3037;
A61F 2002/3038; A61F 2002/30387;
A61F 2002/30392; A61F 2002/30395;
(Continued)

(56) References Cited

U.S. PATENT DOCUMENTS 7,608,080 B2 * 10/2009 Shipp .................... A61F 2/4611
606/99
9,655,735 B2 * 5/2017 Baynham ................ A61F 2/442
(Continued)

*Primary Examiner* — Pedro Philogene
(74) *Attorney, Agent, or Firm* — Olive Law Group, PLLC

(57) ABSTRACT

Instruments, kits, and methods are disclosed for installing an implant spacer through an incision and down a surgical corridor. The instruments also serve to align a drill guide and align and insert a spacer stabilizer for stabilization of adjacent bone portions. An inserter instrument comprises an elongated guide bar body having a guide portion for aligning instruments with said spacer and for introducing a stabilizer to secure the spacer in a predetermined position between the bone portions. In preferred embodiments a stabilizer implant portion comprising a base wall separated by a retaining member by a web wall is introduced into a pre-bored hole in a bone and secured with a stabilizer anchor extending through a central bore. Included is a retractable graft block for securing graft material within an aperture of a spacer during insertion of the spacer.

21 Claims, 21 Drawing Sheets

Related U.S. Application Data continuation-in-part of application No. 13/347,526, filed on Jan. 10, 2012, now Pat. No. 9,486,324, and a continuation-in-part of application No. 12/692,503, filed on Jan. 22, 2010, now Pat. No. 8,157,865.

(60) Provisional application No. 62/249,985, filed on Nov. 3, 2015, provisional application No. 61/862,671, filed on Aug. 6, 2013, provisional application No. 61/146,616, filed on Jan. 22, 2009.

(51) Int. Cl.
| | | |
|---|---|---|
| *A61F 2/44* | (2006.01) | |
| *A61F 2/46* | (2006.01) | |
| *A61B 17/56* | (2006.01) | |
| *A61B 17/00* | (2006.01) | |
| *A61F 2/30* | (2006.01) | |
| *A61F 2/28* | (2006.01) | |
| *A61B 17/16* | (2006.01) | |
| *A61B 17/86* | (2006.01) | |

(52) U.S. Cl.
CPC ....... *A61B 17/1615* (2013.01); *A61B 17/1671* (2013.01); *A61B 17/1757* (2013.01); *A61B 17/8605* (2013.01); *A61B 2017/0046* (2013.01); *A61B 2017/564* (2013.01); *A61F 2/4465* (2013.01); *A61F 2002/2835* (2013.01); *A61F 2002/3037* (2013.01); *A61F 2002/3038* (2013.01); *A61F 2002/30133* (2013.01); *A61F 2002/30135* (2013.01); *A61F 2002/30136* (2013.01); *A61F 2002/30164* (2013.01); *A61F 2002/30166* (2013.01); *A61F 2002/30172* (2013.01); *A61F 2002/30182* (2013.01); *A61F 2002/30197* (2013.01); *A61F 2002/30387* (2013.01); *A61F 2002/30392* (2013.01); *A61F 2002/30395* (2013.01); *A61F 2002/30401* (2013.01); *A61F 2002/30504* (2013.01); *A61F 2002/30507* (2013.01); *A61F 2002/30518* (2013.01); *A61F 2002/30596* (2013.01); *A61F 2002/30598* (2013.01); *A61F 2002/30616* (2013.01); *A61F 2002/30883* (2013.01); *A61F 2002/30884* (2013.01); *A61F 2002/30892* (2013.01); *A61F 2002/4475* (2013.01); *A61F 2310/00017* (2013.01); *A61F 2310/00023* (2013.01); *A61F 2310/00179* (2013.01)

(58) Field of Classification Search
CPC .. A61F 2002/30401; A61F 2002/30504; A61F 2002/30507; A61F 2002/30518; A61F 2002/30596; A61F 2002/30598; A61F 2002/30616; A61F 2002/30883; A61F 2002/30884; A61F 2002/30892; A61F 2002/4475; A61F 2310/00017; A61F 2310/00023; A61F 2310/00179; A61B 17/1757; A61B 17/7076; A61B 2017/0046; A61B 2017/564
USPC ............ 606/246–279, 86 R, 92–96, 99, 100; 623/17.11–17.16
See application file for complete search history.

(56) References Cited

U.S. PATENT DOCUMENTS

| | | | |
|---|---|---|---|
| 2003/0149438 A1* | 8/2003 | Nichols | A61B 17/025 606/99 |
| 2009/0012527 A1* | 1/2009 | Mignucci | A61F 2/4611 606/99 |
| 2009/0209967 A1* | 8/2009 | Evans | A61F 2/4611 606/99 |
| 2010/0204737 A1* | 8/2010 | Bae | A61B 17/846 606/279 |
| 2012/0215313 A1* | 8/2012 | Saidha | A61F 2/4455 623/17.16 |
| 2018/0071108 A1* | 3/2018 | Glerum | A61F 2/447 |

* cited by examiner

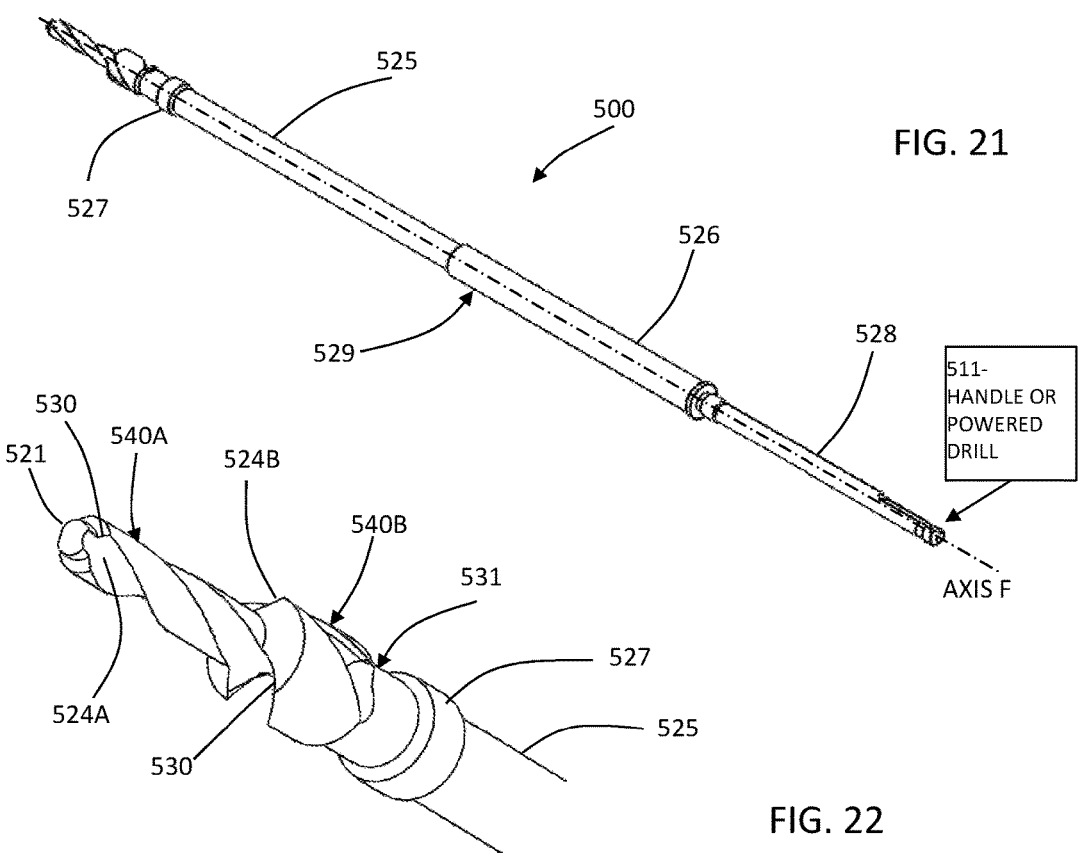
FIG. 21
FIG. 22
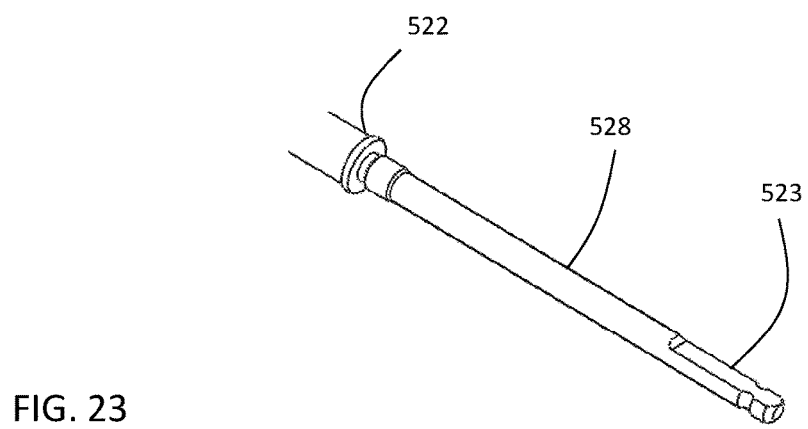
FIG. 23

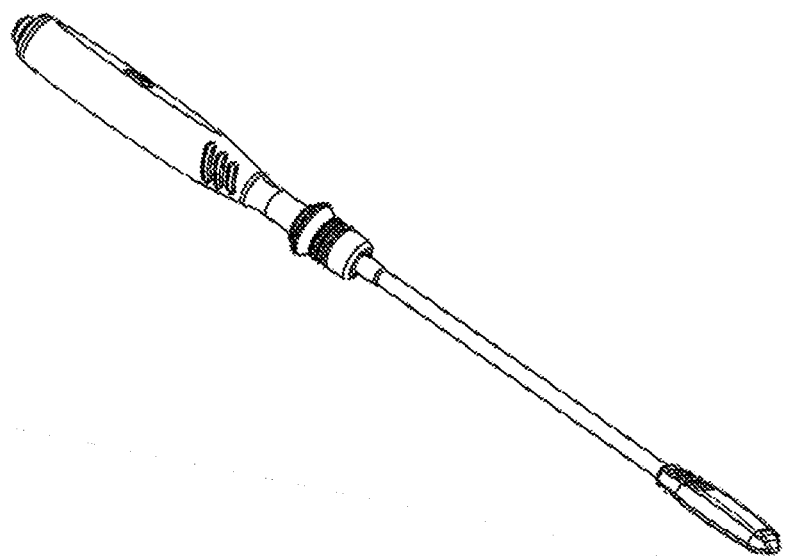
FIG. 26
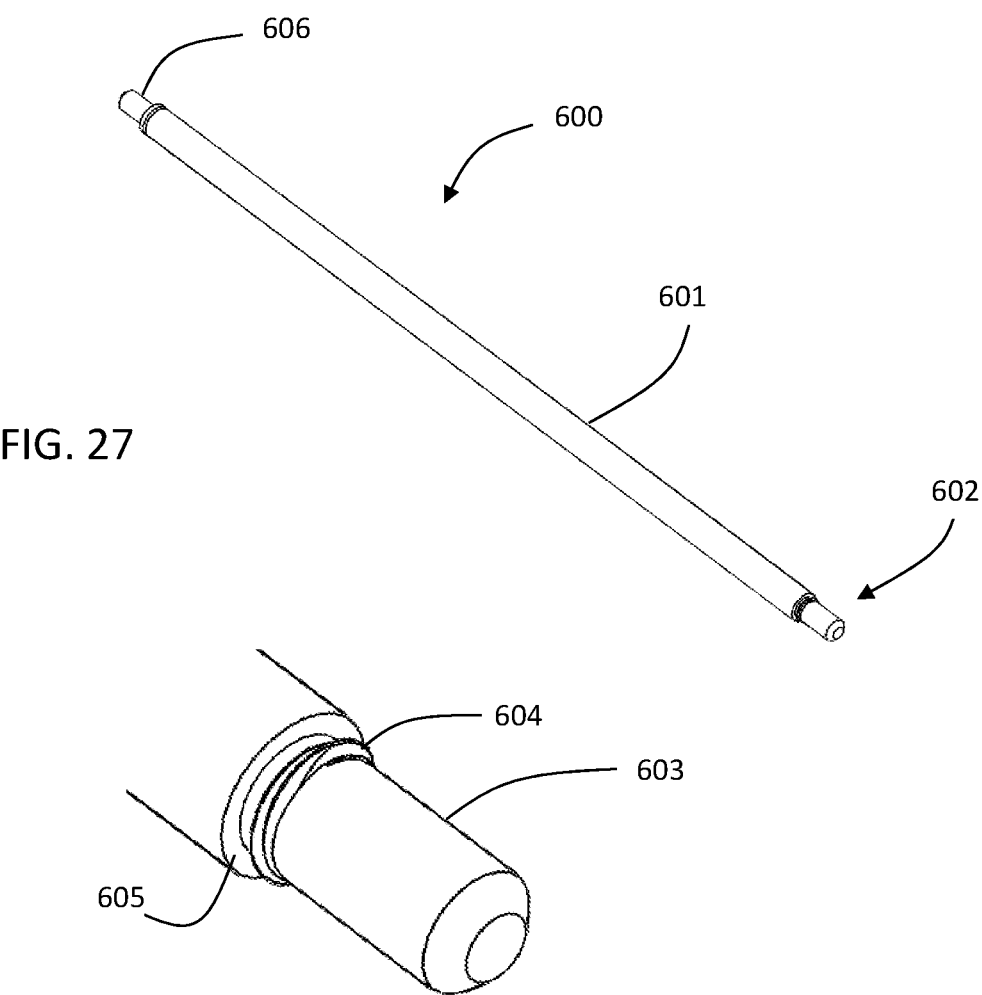
FIG. 27
FIG. 28

BONE STABILIZATION IMPLANTS, INSTRUMENTS, AND METHODS

CROSS REFERENCE TO RELATED APPLICATIONS

This application is a Continuation-In-Part of application Ser. No. 14/453,520 filed Aug. 6, 2014 which is a Continuation-In-Part of application Ser. No. 13/347,526 filed Jan. 10, 2012 which claims priority to Continuation-In-Part application Ser. No. 12/692,503 filed on Jan. 22, 2010, now U.S. Pat. No. 8,157,865 and provisional application No. 61/431,235 filed on Jan. 10, 2011. This application also claims priority to Provisional Patent Application 62/249,985 filed Nov. 3, 2015 and through the above-noted Ser. No. 14/453,520 claims priority to Provisional Patent Application No. 61/862,671 filed Aug. 6, 2013, and through the above-noted Ser. No. 12/692,503 claims priority to Provisional Patent Application No. 61/146,616 filed Jan. 22, 2009, the entire disclosures of which are hereby incorporated by reference and relied upon.

BACKGROUND OF THE INVENTION

Field of the Invention

The invention relates generally to implants, instruments, instrument kits, and methods for stabilizing bone segments or portions of bone, and more particularly to securing interbody spacers between adjacent bones including bones of the human spine.

Description of Related Art

Numerous medical procedures are performed that require the stabilization of adjacent bone portions through the securing of an interbody spacer to the adjacent bone portions. Examples of these spacers are those known in the field as interbody cages, corpectomy cages, osteotomy wedges, joint spacers, bone void fillers, etc.

As one example, spacers are used to fuse joints. Spacers are also used to repair complex fractures where bone is missing and in bone regions where there are otherwise voids, as when a tumor and adjacent bone are removed. Spacers are also used in the performance of osteotomies by placing the spacers between adjacent bone portions to perform a wedging action, as to straighten a bone. This list is not exhaustive of the medical procedures that require the placement of a spacer between adjacent bone portions.

In each procedure, the spacer placed between the bone portions is required to be rigidly joined to the adjacent bone portions. A multitude of different apparatus have been devised for this purpose, with many relying on the use of one or more screws. While screws can be effective for this purpose, they are often limited in the sense that they do not afford stability in all dimensions required to effect the optimal or desired rigidity.

Spacers are commonly used in spinal repair and reconstruction. The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibro-cartilaginous bodies.

The intervertebral fibro-cartilages are also known as intervertebral disks and are made of a fibrous ring filled with pulpy material. The disks function as spinal shock absorbers and also cooperate with synovial joints to facilitate movement and maintain flexibility of the spine. When one or more disks degenerate through accident or disease, nerves passing near the affected area may be compressed and are consequently irritated. The result may be chronic and/or debilitating back pain. Various methods and apparatus have been designed to relieve such back pain, including spinal fusion using a suitable graft or interbody spacer using techniques such as Anterior Lumbar Interbody Fusion (ALIF), Posterior Lumbar Interbody Fusion (PLIF), or Transforaminal Lumbar Interbody Fusion (TLIF) surgical techniques. The implants used in these techniques, also commonly referred to as vertebral body replacement (VBR) devices, are placed in the interdiscal space between adjacent vertebrae of the spine.

Ideally, a fusion graft should stabilize the intervertebral space and become fused to adjacent vertebrae. Moreover, during the time it takes for fusion to occur, the graft should have sufficient structural integrity to withstand the stress of maintaining the space without substantially degrading or deforming and have sufficient stability to remain securely in place prior to actual bone ingrowth fusion.

One significant challenge to providing fusion graft stability (prior to actual bone ingrowth fusion) is preventing spinal extension during patient movement. Distraction of the vertebral space containing the fusion graft may cause the graft to shift or move, disrupting bone ingrowth fusion and causing pain.

Generally, existing spinal fusion technology has been limited or lacking in certain respects. Among the limitations of certain of these systems is the requirement that complicated steps be performed to effect their use. Others of these systems lack the optimal multi-dimensional stability, while others are less than desirable because they utilize components that project to externally of one or more of the bone portions between which the spacer is located.

The systems that rely upon traditional screw use normally have such limitations. Generally these systems do not effectively allow compression forces to be generated between the spacers and adjacent bone portions. Further, while the screws stabilize the bone-spacer junction in one plane, that is normally flexion-extension, they do not control bending in planes orthogonal to the plane of the screw, that is normally side-to-side bending.

A further problem with existing systems is that parts typically are not locked and are thus prone to working loose. Traditional bone screws often loosen over time.

The spacers and features of the spacer for joining it to the bone portions are typically inserted within surgical corridors offering limited access and vision. A further problem is that existing systems do not have instrumentation that is intuitive and well suited for performing the surgical procedure within this corridor. Instruments that are not intuitive make the surgery difficult and increases the potential for injury to the patient.

The medical field is constantly seeking system designs that might be efficiently and consistently installed and that, most significantly, will effect the desired fusion in a manner that will be safe and reliable for the patient.

BRIEF SUMMARY OF THE INVENTION

In one form, the invention is directed to a method for stabilizing first and second adjacent bone portions. The method includes the steps of: providing a spacer; providing a stabilizer, with the spacer and stabilizer configured to be movable guidingly, one relative to the other, between a pre-assembly relationship and an operative relationship; and placing the spacer and stabilizer into an operative relationship with the first and second adjacent bone portions by: a) placing the spacer between the first and second adjacent bone portions; b) directing the stabilizer into the first bone portion; and c) changing the spacer and stabilizer from their pre-assembly relationship into their operative relationship by driving a stabilizer anchor such as a bone screw through a portion of the stabilizer and further threading the bone screw into one of the bones to be stabilized. As an incident of the spacer and stabilizer being changed from their pre-assembly relationship into the operative relationship with each other and the first and second bone portions, the spacer, stabilizer, stabilizer anchor, and first bone portion cooperate to cause the first bone portion and spacer to be secured against each other.

In one form, the step of providing a stabilizer involves providing a stabilizer with a body having first and second spaced walls joined by a web. The first and second spaced walls respectively have first and second surfaces that generally face each other.

In one form, the method further includes the step of pre-forming a first channel in the first bone portion and the step of directing the stabilizer into the first bone portion involves moving the second wall guidingly in the first channel between a first position and a second position. The second wall is in the second position with the spacer and stabilizer in the operative relationship with the first and second adjacent bone portions.

In one form, the method includes the step of pre-forming a first channel having a step in the bone wherein the distal portion of the channel has a smaller diameter for insertion of an anchor such as a bone screw and a larger diameter portion proximal the step for housing a retaining member portion of the stabilizer.

In one form, the spacer has a first surface that faces a first surface on the first bone portion with the spacer between the first and second bone portions and the stabilizer web has a sharp leading edge. The step of directing the stabilizer into the first bone portion includes the step of causing the sharp leading edge on the web to cut through the first bone portion between the first channel and first surface on the first bone portion.

In one form, the step of providing a stabilizer involves providing a stabilizer having a length, with the second wall having a lengthwise axis. The second surface has a convex curvature, as seen in cross-section taken transversely to the length of the stabilizer, with a radius at or adjacent to the lengthwise axis of the second wall. The stabilizer further has a leading end with a tapered surface portion that is angled between the leading end and the second surface. The spacer is placed between the first and second bone portions before the stabilizer is directed into the first bone portion. As an incident of the stabilizer being changed from its first position into its second position, a stabilizer anchor such as a bone screw is passed through a retaining member portion of the stabilizer and threaded into the bone. A lead preferably in the form of a tapered surface bears against the first bone portion and progressively wedges the first bone portion towards the spacer.

In one form, the first and second bone portions are adjacent first and second vertebrae. The spacer has oppositely facing first and second surfaces. The first vertebra has a first endplate with a first surface facing the first surface on the spacer. The first endplate has a first dimension parallel to the length of the stabilizer with the spacer and stabilizer in their operative relationship. The step of providing a stabilizer involves providing a stabilizer wherein the second surface on the stabilizer applies a force on the first bone portion over a majority of the first dimension of the first surface of the first endplate that urges the first endplate surface against the first spacer surface.

In one form, the step of placing the spacer and stabilizer into operative relationship with the first and second adjacent bone portions involves causing a part of the first bone portion and a part of the spacer to be compressively maintained between the first and second stabilizer surfaces.

In one form, the step of directing the stabilizer into the first bone portion involves advancing the stabilizer guidingly in a path in a first direction. The method further includes the step of reconfiguring the stabilizer, with the spacer and stabilizer in the operative relationship with the first and second adjacent bone portions, into a locked state to block movement of the stabilizer relative to the first bone portion oppositely to the first direction.

In one form, the stabilizer has a central bore and the step of reconfiguring the stabilizer from the first state into the locked state involves advancing a stabilizer anchor through the central bore from a first position into a second position wherein a stabilizer anchor is in the form of a screw threaded into bone.

In one form, the step of providing a stabilizer involves providing a stabilizer with a movable stabilizer screw, and the step of reconfiguring the stabilizer involves moving the stabilizer screw from a first position into a second position as an incident of which a screw head secures the stabilizer within a bore created in the bone.

In one form, the step of providing a stabilizer involves providing a stabilizer that is turned about an axis relative to the second wall to change the stabilizer screw between its first and second positions.

In one form, the step of reconfiguring the stabilizer involves providing a stabilizer and a stabilizer anchor whereby advancing the stabilizer anchor from a first position to a second position causes the stabilizer anchor to be threaded into a portion of the stabilizer.

In one form, the step of providing a spacer involves providing a spacer with a channel and the step of changing the spacer and stabilizer from their pre-assembly relationship into their operative relationship involves moving a part of the stabilizer guidingly within the channel.

In one form, the steps of providing a spacer and stabilizer involve providing a spacer and stabilizer each with a blocking surface, which blocking surfaces abut to block the spacer and stabilizer from moving out of their operative relationship.

In one form, the steps of providing a spacer and stabilizer involve providing a spacer and stabilizer each with a blocking surface, which blocking surfaces are brought into confronting relationship as an incident of the spacer and stabilizer being changed from their pre-assembly relationship into their operative relationship.

In one form, the method further includes the step of reconfiguring one of the spacer and stabilizer with the spacer and stabilizer in their operative relationship to thereby place the blocking surfaces on each of the spacer and stabilizer in confronting relationship.

In one form, the steps of providing a spacer and stabilizer involve providing a deflectable tab defining the blocking surface on one of the spacer and stabilizer which deflects in one direction as the spacer and stabilizer are changed from their pre-assembly relationship into their operative relationship and is moved oppositely to the one direction under a restoring force to place the blocking surface on the one of the spacer and stabilizer into confronting relationship with the blocking surface on the other of the spacer and stabilizer as an incident of the spacer and stabilizer realizing the operative relationship.

In one form, the step of providing a stabilizer involves providing a stabilizer wherein the deflectable tab is on the first wall of the stabilizer.

In one form, the step of providing a stabilizer involves providing a stabilizer wherein the first wall and web on the stabilizer cooperatively define a "T"-shaped portion.

In one form, the step of providing a spacer involves providing a spacer with a "T"-shaped channel that is complementary to the "T"-shaped portion of the stabilizer, and the step of changing the spacer and stabilizer from their pre-assembly relationship into their operative relationship involves moving the "T"-shaped portion of the stabilizer guidingly within the "T"-shaped channel.

In one form, the step of providing a stabilizer involves providing a stabilizer with the second surface on the second wall having a convexly curved shape.

In one form, the step of providing a stabilizer involves providing a stabilizer with the second wall on the stabilizer having a cylindrical shape.

In one form, the step of providing a stabilizer involves providing a stabilizer wherein the first wall and web are substantially flat and cooperatively define a "T"-shaped portion. The second surface on the second wall has a convexly curved shape.

In one form, the method further involves the step of reconfiguring the stabilizer from a first state, with the spacer and stabilizer in the operative relationship with the first and second adjacent bone portions, into a locked state by moving a part of the stabilizer anchor portion into the first bone portion.

In one form, the stabilizer is directed into the bone portion before the spacer and stabilizer are changed from their pre-assembly relationship into their operative relationship.

In one form, the method further includes the step of providing a second stabilizer and connecting the second stabilizer to each of the spacer and the second bone portion.

In one form, the method further includes the step of reconfiguring the stabilizer after it has been changed into the locked state back into the first state and thereafter separating the stabilizer and spacer from the first and second bone portions.

In one form, the method further includes the steps of providing a guide structure on the spacer and using the guide structure to pre-form the first channel in the first bone portion.

In one form, the step of moving the part of the stabilizer forcibly against the first bone portion involves the step of moving the part of the stabilizer forcibly against the first bone portion in a manner so as to thereby urge the first bone portion and spacer against each other.

In one form, the step of providing a spacer involves providing a spacer with first and second spaced bores. The method further includes the step of providing an auxiliary tool that is used in conjunction with the spacer by connecting the auxiliary tool using at least one of the first and second bores.

In one form, the method further includes the step of connecting the auxiliary tool to the spacer by placing first and second connectors on the auxiliary tool one each into the first and second bores.

In one form, the method further includes the step of connecting the auxiliary tool to the spacer by using either one, but only one, of the first and second bores.

In one form, the steps of providing a spacer and stabilizer include providing first and second deflectable tabs each defining a blocking surface on at least one of the spacer and stabilizer that each deflects in a direction as the spacer and stabilizer are changed from the pre-assembly relationship into the operative relationship, and are moved oppositely to their deflecting direction under restoring forces to place each of the blocking surfaces separately into confronting relationship with a blocking surface on the spacer or stabilizer as an incident of the spacer and stabilizer realizing the operative relationship.

In one form, the step of placing a spacer and stabilizer in operative relationship with the first and second bone portions involves moving the spacer and stabilizer substantially only in a single plane and parallel to a single line.

In one form, the step of preparing the spacer with graft includes covering bone graft in a graft aperture within the spacer to prevent unintentional fallout of the bone graft while packing bone graft in the spacer aperture and during insertion of the spacer between bone portions.

In one form, the step of preparing the spacer with graft includes inserting a graft block into an anchor portion of the spacer wherein a paddle extending from the graft block covers a graft aperture on the spacer to prevent unintentional fallout of bone graft packed within the graft aperture.

In one form, the step of preparing the spacer with graft includes inserting a plurality of graft blocks into one or more anchor portions of the spacer wherein a plurality of paddles on the graft blocks cause the bone graft to substantially encapsulate the bone graft within the graft aperture.

In one form, during the step of inserting the spacer between the bone portions, the graft blocks are retracted therein placing the spacer's graft aperture in direct communication with the bone portions.

In one form, the step of inserting the spacer between the bone portions includes abutting a stop face on the graft block against the bone portions preventing further advancement of the graft block.

In one form, the step of inserting the spacer between the bone portions includes the step of one or more graft blocks retracted from the incision site.

In one form, the step of inserting a drill guide includes joining the tip of a drill guide with an anchor portion of a spacer and advancing the drill guide to a predetermined position against a bone portion.

In one form, the step of creating a hole within a bone portion includes advancing a bone drill down a drill guide and into the bone portion.

In one form, the step of creating a hole within a bone portion includes advancing a bone drill having a plurality of step diameters into the bone portion.

In one form, the step of inserting a stabilizer includes releasably securing a stabilizer inserter to a proximal end of a stabilizer.

In one form, the step of inserting a stabilizer includes aligning a base wall nose within a spacer channel or spacer inserter tool channel and advancing the stabilizer into the spacer by applying directed force to a stabilizer inserter.

In one form, the step of inserting a stabilizer includes advancing the stabilizer until the stabilizer reaches a predetermined position with respect to the spacer and locking the stabilizer in place with a stabilizer anchor. In one form, the step of inserting a stabilizer includes removing a stabilizer inserter from the incision site.

In one form, the step of placing the stabilizer in an operative relationship includes inserting the tip of a drill guide into a spacer channel or spacer inserter channel and advancing the drill guide to the stabilizer.

In one form, the step of placing the stabilizer in an operative relationship includes releasably securing a stabilizer screw driver tool to a stabilizer screw and advancing the stabilizer screw into the stabilizer.

In one form, the invention is directed to the combination of a stabilizer and spacer. The spacer can be placed between first and second adjacent bone portions and has oppositely facing surfaces. The stabilizer is movable guidingly relative to the spacer in a first path in a first direction: a) from a position wherein the stabilizer is in a pre-assembly relationship with the spacer; and b) into a position wherein the stabilizer is in an operative relationship with the spacer. The stabilizer is capable of being directed in the first direction while being moved in the first path relative to the spacer into one of the first and second bone portions so as to urge a surface of the one bone portion forcibly against one of the spacer surfaces with the spacer and stabilizer in operative relationship with each other and the first and second adjacent bone portions. The stabilizer has a body including first and second spaced walls joined by a web. The first and second spaced walls respectively have first and second surfaces that face each other. The second wall has a leading end and a surface portion that is angled with respect to the first path to produce a wedging action against the one bone portion as the stabilizer is advanced in the first direction in the first path into the one bone portion. The wedging action causes a part of the one bone portion and a part of the spacer to be urged towards each other as the spacer and stabilizer are moved into operative relationship with each other and the first and second adjacent bone portions.

In one form, the stabilizer has a length and a lengthwise axis. The first path is substantially straight along a first line and the second surface has a convex curvature as seen in cross-section taken transverse to the length of the stabilizer with a radius that is centered on a line parallel to the lengthwise axis of the stabilizer.

In one form, the stabilizer has a lead defining the tapered surface portion that is angled with respect to the central axis of the stabilizer.

In one form, the second wall has a cylindrical shape and the lead defines the surface portion that tapers between a leading end of the second wall and the second surface.

In one form, the combination further includes a stabilizer anchor screw that is selectively movable relative to the stabilizer to thereby change the stabilizer from the first state into the locked state.

In one form, the first wall and web are substantially flat and cooperatively define a "T"-shaped portion. The spacer has a "T"-shaped channel that cooperates with the "T"-shaped portion of the stabilizer to guide relative movement between the pre-assembly and operative relationships.

In one form, the second wall has a substantially cylindrical shape that defines the second surface.

In one form, the first surface resides in a first plane and the cylindrical shape has a central axis. The first plane and central axis of the cylindrical shape are substantially parallel.

In one form, the first surface resides in a first plane and the cylindrical shape has a central axis and the first plane and central axis of the cylindrical shape are at an angle with respect to each other.

In one form, the spacer has a channel to guide the stabilizer as the spacer and stabilizer are relatively moved between their pre-assembly and operative relationships. The spacer has a stop portion that abuts the stabilizer moving in the first direction so that the spacer and stabilizer can be consistently placed in their operative relationship.

In one form, the spacer and stabilizer have cooperating blocking surfaces that abut to block the spacer and stabilizer from moving out of their operative relationship.

In one form, the blocking surfaces contact each other as an incident of the spacer and stabilizer realizing the assembly relationship.

In one form, one of the blocking surfaces is on a movable tab on one of the spacer and stabilizer. The movable tab is deflected in one direction as the spacer and stabilizer are moved from their pre-assembly relationship toward their operative relationship and moves under a restoring force oppositely to the one direction upon the operative relationship between the spacer and stabilizer being realized.

In one form, one or more channels within a spacer for receiving a stabilizer implant portion are positioned anterior to a central bone graft opening.

In one form, one or more channels within a spacer for receiving a stabilizer implant portion are positioned posterior to a central bone graft opening.

In one form, the second wall has a cylindrical shape with a central axis. The combination further includes a drill guide on the spacer and a drill that is movable controllably along the drill guide parallel to a central axis of the drill. The spacer has a third surface to which the first surface of the stabilizer abuts with the spacer and stabilizer in their operative relationship. In some forms, a first distance between the central axis of the drill on the drill guide and the third surface is greater than a second distance between the central axis of the second wall and the first surface.

In one form, the first distance is greater than the second distance by on the order of 0.5 mm.

In one form an auxiliary tool is a cage or spacer inserter tool.

In one form, the spacer inserter tool comprises a longitudinal guide to direct the stabilizer through an incision and into an anchor portion of the spacer. In one form the longitudinal guide directs axillary tools into or in alignment with an anchor portion of the spacer.

In one form, the longitudinal guide comprises opposing channels.

In one form, the opposing channels are in the form of T-shaped slots.

In one form, the body of the spacer inserter tool comprises a shaft aperture.

In one form, the spacer inserter tool houses a locking shaft for securing the spacer to the spacer inserter tool.

In one form, the locking shaft resides in a shaft aperture having an elongate axis formed within the spacer inserter tool.

In one form, the elongate axis of the shaft aperture formed within the spacer inserter tool for housing the locking shaft is parallel to an elongate axis of the longitudinal guide.

In one form, the spacer inserter tool comprises a handle portion for grasping by the user for controlling the spacer inserter tool.

In one form, an elongate axis of the handle portion is generally perpendicular to an elongate axis of a guide bar body portion of the spacer inserter tool.

In one form, the locking shaft includes an impact fitting. The impact fitting may be used to tap the spacer inserter and spacer into the intervertebral space.

In one form, an auxiliary tool is a graft blocker for containing bone graft or bone substitute within the spacer during insertion of the spacer.

In one form the graft blocker comprises a paddle portion for covering an opening within the spacer where graft is contained during implant insertion.

In one form, the graft blocker comprises one or more channel locks for guiding and sliding engagement of the graft blocker with the longitudinal guide of the spacer inserter tool and for sliding engagement with an aligned anchor portion within the spacer.

In one form, the graft blocker includes an arm for the user to control the graft blocker from outside the incision while the spacer is inserted to a predetermined position between the bone portions.

In one form, the graft blocker includes a stop face that abuts the bone portions and causes retraction of the graft blocker as the spacer is inserted between the bone portions.

In one form, the auxiliary instruments comprise cleaning or access apertures for cleaning the instruments.

In one form, the auxiliary instrument is a drill guide for guiding a drill to predetermined location within a bone portion.

In one form, the drill guide includes a drill guide cylinder for guiding a drill within the drill guide.

In one form, the drill guide comprises a drill guide tip that is insertable into an anchor portion of a spacer to ease insertion of the drill guide into the spacer.

In one form, the drill guide includes a handle portion for the user to control position of the drill guide within the incision.

In one form, the drill guide includes a base wall and a web wall for aligning the drill guide within the longitudinal guide of the spacer inserter tool or within the anchor portion of the spacer.

In one form, the drill guide includes a drill guide stop to align the relative depth of drill guide with the spacer inserter tool.

In one form, a kit is provided comprising various implants and instruments described herein for use in a surgery.

BRIEF DESCRIPTION OF SEVERAL VIEWS OF THE DRAWINGS

FIG. 21 is a top perspective view of a preferred embodiment of a bone drill.

FIG. 22 is a partial end view of the bone drill of FIG. 21.

FIG. 23 is a partial end view of the drive end of the bone drill of FIG. 21.

FIG. 26 is a top perspective view of a trial spacer from the prior art.

FIG. 27 is a top perspective view of a preferred embodiment of a stabilizer inserter with a stabilizer inserter handle portion removed.

FIG. 28 is a partial close up view of the insertion tip of the stabilizer inserter of FIG. 27.

DETAILED DESCRIPTION OF THE INVENTION

Embodiments of the invention will now be described with reference to the Figures. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein.

Figure 1:
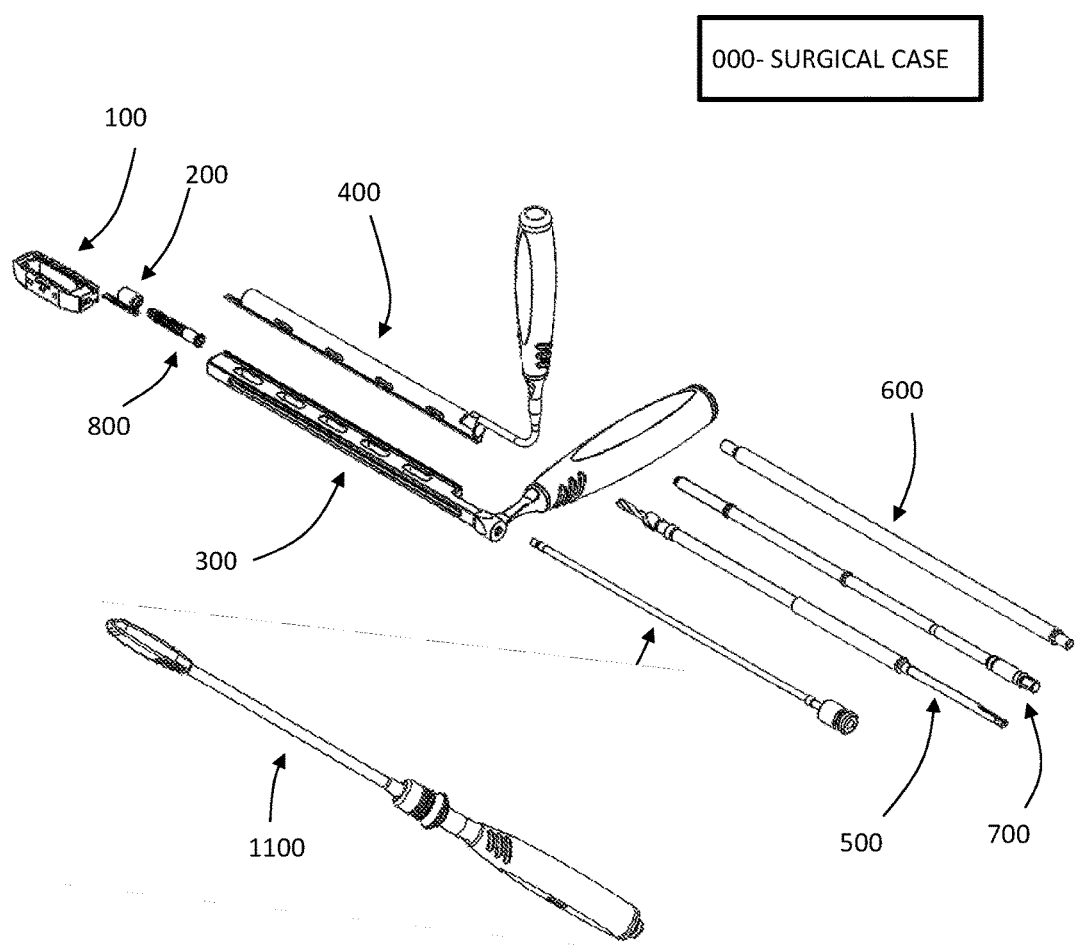
FIG. 1 is a perspective view of one embodiment of a surgical kit comprising both instruments and implants portions used for the stabilization of bone portions.

In a preferred embodiment, a kit containing at least some of the implants and instruments for inserting the implant between a plurality of bone portions is illustrated in FIG. 1. In some embodiments, the implants and instruments are provided in one or more surgical cases 000. The kit generally comprises an implant comprised of a cage or spacer 100 portion and a stabilizer anchor portion. In preferred forms as illustrated in FIG. 1, the stabilizer anchor portion comprises a stabilizer 200, and a stabilizer anchor 800 typically in the form of a bone screw. The instruments may comprise; a spacer inserter 300 portion, spacer locking shaft 302, a drill guide 400 portion, a bone drill 500, a stabilizer inserter 600, a stabilizer screw inserter 700, a graft block 1000 (FIG. 29), and a trial spacer 1100. One or more of these implants or instruments may be included in a surgical case illustrated schematically in FIG. 1.

According to one embodiment, a spacer 100 is illustrated in FIGS. 2-5. The spacer, also known as a cage 100 comprises a body 190 with first side surface 160, and second side surface 170, a first channel 155, and a second channel 165, a proximal face 140 and a distal face 150, a first and second opposite surfaces 110, 120, an opening 132 for graft or other bone substitute material, and protrusions in the form of teeth 135.

FIGS. 2, 3, 6-8, illustrate a preferred embodiment of a stabilizer 200. The stabilizer 200 has a base wall 210, a web wall 220, and a retaining member 230 preferably in the form of a cylinder (cylindrical wall) with a sharp leading edge 240 to cut bone against which it is advanced. The stabilizer 200 has self-retaining clips 250 preferably in the form of barbs/tabs.

The spacer body 190 has a height "h" sized to fit within a portion of the intervertebral disc space. The intervertebral space, as defined by the shape/footprint of the vertebral body endplates, is generally "D"-shaped and the implant spacer/cage 100 preferably has an outer profile shape to fill substantially the entire disc space. Interbody implants may take streamlined profiles, as between anterior and posterior sides, to provide less invasive entry into the intervertebral space during surgery and to help accommodate to the surgical approach. Regardless of their configuration, it is desirable that the combined spacer and stabilizer have a "zero-profile", meaning that no part of either component protrudes from the space between adjacent bone portions. For example, rectangular or banana-shaped profiles may be used such as illustrated in the embodiment in FIG. 4 since they are thinner in a width dimension, thereby requiring a smaller/less invasive path of entry into the intervertebral disc space. In one preferred form again illustrated in FIG. 4, an anterior wall portion 175 of the implant, that is part of a continuous profile wall 180 and defines the first side surface 160, has a gentle convex arc similar to the anterior wall of the vertebral body and a predetermined width between the side surfaces 160 and 170 to facilitate minimally invasive entry along an axis or line generally parallel to the lengths of the first channel 155 and second channel 165.

The outer profile wall 180 defines one or more openings 132, 195 for packing bone graft or other bone substitutes to ultimately facilitate fusion between vertebral bodies. The opening 132 is completely surrounded by the wall 180 to hold the graft material within the body 190. The wall 180 may have openings partially or fully therethrough for packing graft. As further illustrated in FIG. 4, two graft apertures sometimes termed openings 195 are formed within the wall 180 and can be utilized for adding additional graft or hydration to the graft within the opening 132.

A proximal face 140 of wall 180 of spacer 100 incorporates features for the attachment of one or more auxiliary instruments utilized to install the spacer 100 within an intervertebral space. In this embodiment, instrument attachment structure is in the form of two bores 115a, 115b with at least one bore 115a threaded (threads not shown) for attachment to a complementarily-threaded insertion facilitating instrument 300. A second hole 115b may also be threaded, though this is not required, and configured to engage a boss from an insertion instrument 300 as a means to counter torque and therein limit rotation between a cage 100 and insertion instrument 300 to be described later. The instrument attachment portion structure could also be in other forms such as a boss, slot, hole, groove or other feature for an auxiliary instrument to attach. If both bores 115a, 115b are threaded and usable individually to cooperate with the instrument 300, the unused bore 115a, 115b is available as a backup, as in the event one of the holes/bores becomes stripped.

Figure 9:
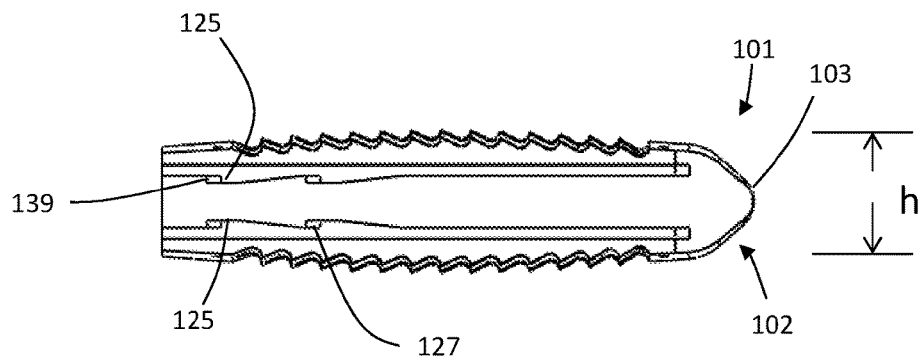
FIG. 9 is a side cross-sectional view of a preferred embodiment of the implant assembly of FIG. 2 (parts removed) according to plane Z of FIG. 2.

A distal face 150 of the body 190 has a nose portion 101 as seen most clearly in the cross-sectional view FIG. 9 are configured to ease entry into the intervertebral space by wedging between vertebral endplates during insertion. This nose portion 101 preferably has a lead in angle taper at 102, in combination with a radiused end 103 defining a blunt arrow or bullet shape. As seen from FIG. 4, the side surfaces 160, 170 may also have a taper or radius 104 where they blend into the radiused end 103 at the distal face 150. This is helpful to wedge soft tissue to the sides of the nose portion 101 during insertion.

In this embodiment, body 190 also has a stabilizer attachment or also termed as anchor portion 145 for securement of stabilizer 200 to cage 100. Anchor portion 145 consists of one, and preferably two, of the aforementioned channels 155, 165 illustrated and otherwise known as keel tracks in this embodiment. Channels 155, 165 are at the site where a stabilizer 200 attaches and is secured to a spacer body 190. Channels 155, 165 extend through surfaces 110 and 120, but in alternative embodiments may be on other surfaces, such as surfaces 160 and 170. The channels 155, 165 are preferably configured wherein one channel 155 is adjacent one bone portion and the other channel 165 is adjacent another bone portion and therebetween spacer 100 resides. Channels 155, 165 in this embodiment are in the form of a T-shaped slot preferably extending along a linear path, although the path could be arced when complemented by an arced stabilizer, or otherwise shaped. The T-shaped slot illustrated is configured to accept and contain a stabilizer, such as the stabilizer 200 with a body 290 illustrated in one form in FIG. 6-8. The stabilizer body 290 has one or more tabs alternatively described as barbs 250 or self-retaining clips.

Figure 4:
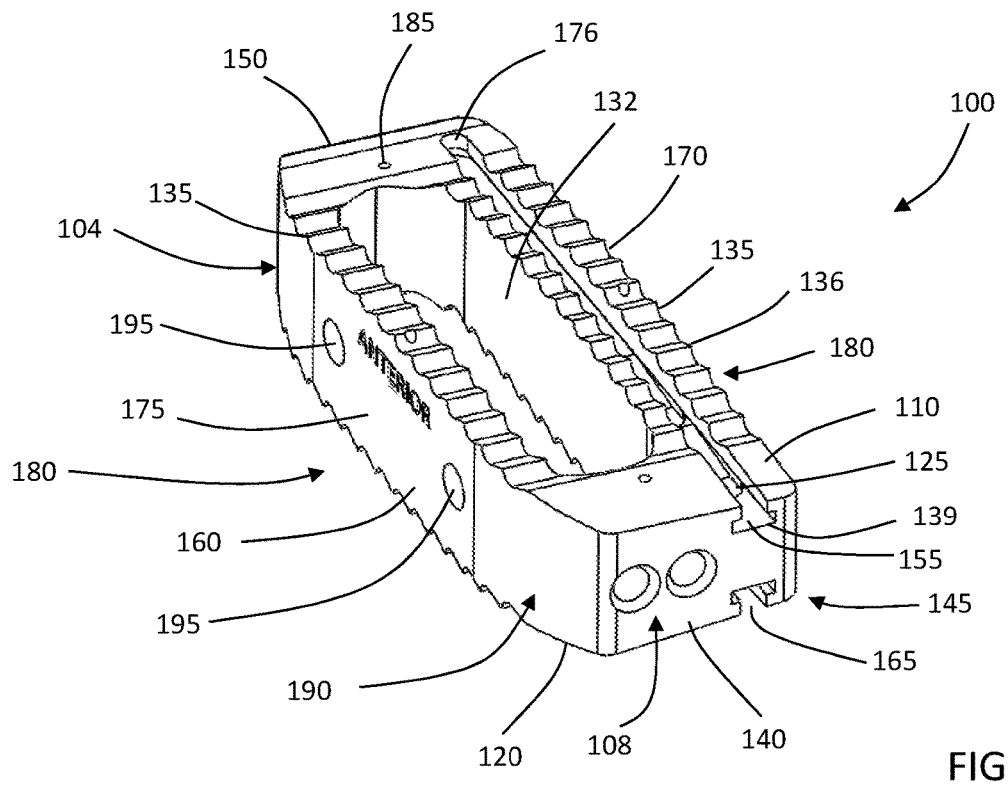
FIG. 4 is a top perspective view of a preferred embodiment of a spacer implant.
Figure 5:
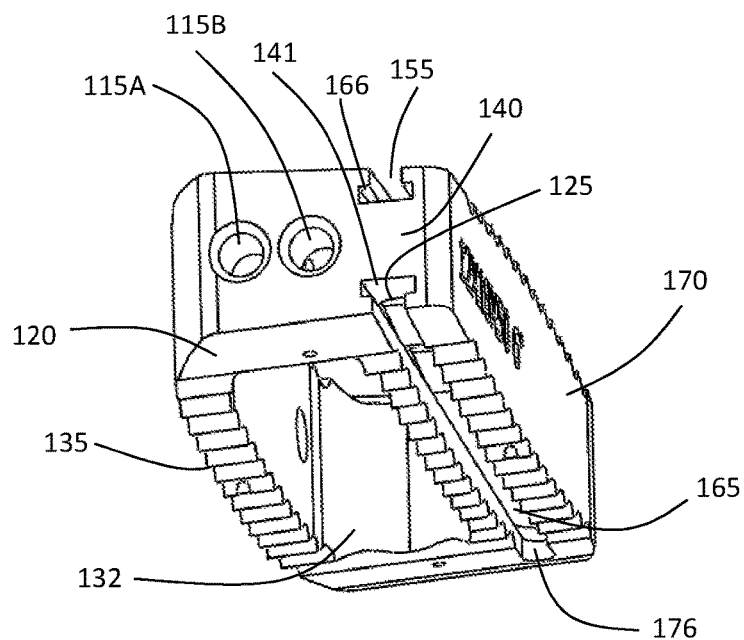
FIG. 5 is a bottom perspective view of the spacer implant illustrated in FIG. 4.

At least one of the first and second channel 155, 165 may include a stabilizer stop portion 176 (FIG. 4-5). Here channels 155, 165 and stop portion 176 extend nearly the length of the implant, however in preferred embodiments the stop portion 176 is positioned further proximally to keep the stabilizer positioned near the proximal end of spacer 100. For example, stop portion 175 may be displaced from proximal face 140 a distance generally equal to the length of web wall 220. Stop portion 176 serves as a termination of the T-shaped channel 155. With a stabilizer body 290 abutted to stop portion 176, the stabilizer 200 is consistently located in its optimal operative relationship to the spacer/cage 100. Stabilizer anchor portion 145 in this embodiment also has a stabilizer lock portion illustrated in FIG. 9 as an undercut region 125 of a channel for receipt of the tabs/barbs 250 on the stabilizer 200.

In FIG. 4, both opposite surfaces 110, 120 of the body 190, on the superior and inferior sides thereof, have channels 155, 165 respectively formed therethrough with each shown as a T-shaped slot. The body 190 of spacer 100 may have one or more marker housings 185 shown here in the form of holes or other recess for the placement of tantalum markers. The markers assist placement of the implant through imaging in the predetermined intervertebral position.

First and second opposite surfaces 110, 120 of implant body 190 ride directly against bone. One or both surfaces 110, 120, as shown, may have one or more of teeth 135 or other protrusions to assist securement of the spacer/cage 100 in its predetermined operative position between the vertebral body bone portions. Each tooth 135 preferably has a peak 136 which may be in the form of a point, or broader surface such as a line, preferably extending generally transverse to the entry line/axis. Each tooth 135 has an entry face that may be sloped to assist moving the implant body 190 into the intervertebral space, and a trailing face that is more steeply sloped to engage a bone portion to prevent the implant body 190 from backing out of the implant space. The teeth 135 are sized deep enough to dig into bone yet shallow enough to avoid substantial loss of intervertebral space following implant insertion once there is subsidence of the teeth or other protrusions 135.

Opposite surfaces 110, 120 are preferably optimized to have sufficient area to adequately support and distribute the forces between the vertebral body endplates while having adequate sized openings 132 for a strong fusion. In turn, wall 180 of the body 190 is thick enough such that it will not buckle under the endplate forces, dependent on the material of construction. The distance h (FIG. 9), between the surfaces 110, 120, is generally equal to the distance between vertebral body endplates when separated by a healthy intervertebral disc. In alternative embodiments, these surfaces are generally flat; however, they are preferably contoured to match the contour of the facing vertebral endplate. An example of the contour can be seen in FIG. 9 with the height bulged near the middle of the cage 100. Similarly, the opposite surface portions 110, 120 may be angled in relation to each other to accommodate to the intervertebral space. The intervertebral space is commonly angled from anterior to posterior. For this reason, some implants, such as the one illustrated in FIG. 4-5, may be angled 6 degrees, as reflected by a slightly greater height on the anterior portion of the implant and sloping to a slightly shorter height on the posterior portion of the implant. This corresponds to a common angulation in the human lumbar spine. In alternative embodiments implants may be angled zero degrees to generally twelve degrees.

The stabilizer 200 functions to: secure body 190 portion in a predetermined operative position relative the adjacent bone portions; assist against back out and over travel of the spacer/cage 100 from this position; and help positively hold surrounding bone close to the spacer 100, thereby facilitating a successful fusion. Wall/retaining member 230 on the stabilizer 200, in the preferred embodiment depicted in FIG. 6, has a cylindrical shape but may take other forms. The stabilizer 200 has a cannulated body 290, generally of the type illustrated in FIGS. 6-8, but could have a multitude of other configurations. In some forms, stabilizer 200 may be integrated with the spacer/cage body 190, but it is preferred that it be a separate component. Stabilizer 200 has a spacer anchor 270 that resides within the stabilizer anchoring portion 145 on the spacer/cage 100 with the spacer/cage 100 and stabilizer 200 operatively connected.

The base wall 210 in this embodiment is flat and configured to be directed into a complementarily-shaped portion of either of channels 155, 165 on body 190. In this case, the base wall 210 and the flat web wall 220 form a "T"-shaped portion to slide in and reside in one of the T-shaped channels 155, 165. The cooperating "T" shapes are such that the spacer anchor 270 can be guided consistently within the channels 155, 165 along the assembly line/axis without excessive resistance but will be closely enough matched to be stabilized in multiple dimensions relative to the spacer/cage 100 thereby eliminating wobble. The lower region of the web wall 220 is preferably thickened where it engages the spacer/cage 100. The exemplary channel 155 is bounded by a channel surface 166.

The complementary shapes of the channels 155, 165 and spacer anchor 270 may take many other forms besides a "T" shape. For example, the base wall 210 could have a triangular, elliptical, or round profile. A leading nose 211 on the base wall 210 serves to lead the base wall 210 into a channel 155, 165 of a stabilizer anchor 145. Similar to the spacer nose 101, it is preferred that the leading nose 211 is at least one of tapered and radiused to ease entry into instrument or implant channels. As seen in cross-section in FIG. 10 and in an operative configuration in FIG. 11, the base wall nose 211 extends ahead of locking sleeve 291 such that the base wall 210 can begin to seat in one of the channels 155, 165 before the locking sleeve 291 is situated to seat in the body of the vertebrae, thereby easing insertion complications.

Figure 7:
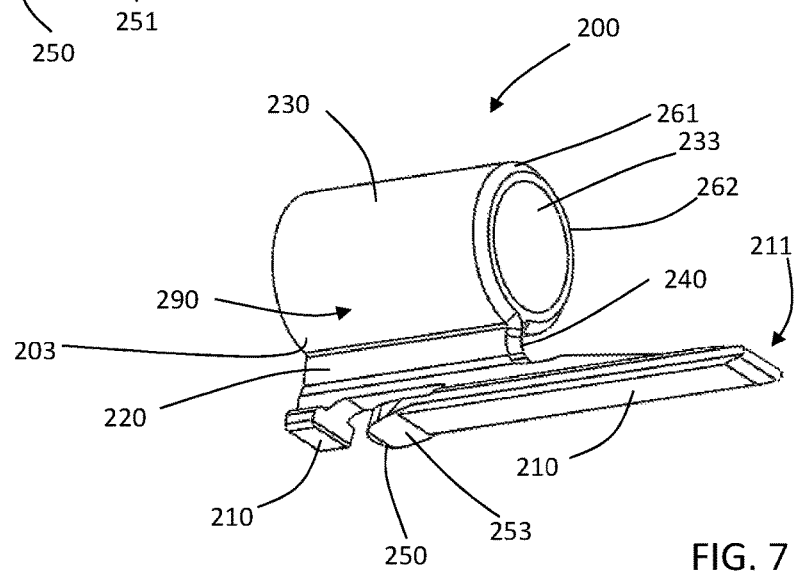
FIG. 7 is a bottom perspective view of the stabilizer portion of a bone stabilization implant assembly illustrated in FIG. 6.
Figure 10:
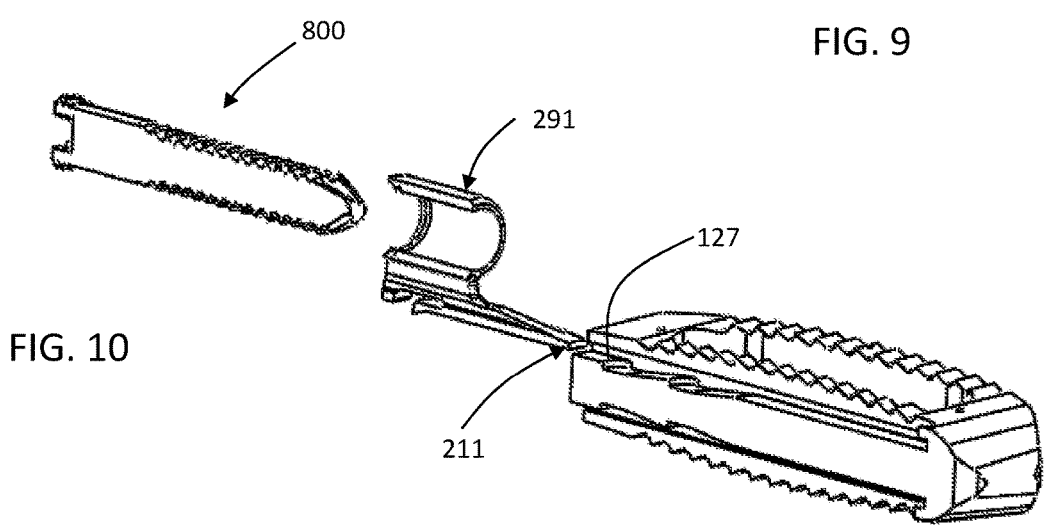
FIG. 10 is a top perspective cross-sectional view of a preferred embodiment of the implant assembly of FIG. 2 according to plane Z of FIG. 2.
Figure 11:
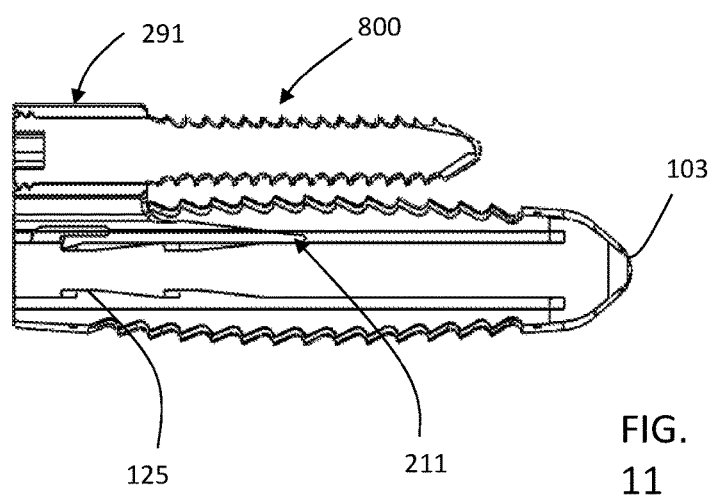
FIG. 11 is a side cross-sectional view of a preferred embodiment of the implant assembly of FIG. 2 according to plane Z of FIG. 2.

Any portion of the spacer anchor 270, but preferably the base wall 210, may include a self-retaining portion. In this embodiment, the base wall 210 has a generally flat wall surface 280 that is abuttable to the spacer/cage surface 166 to prevent pullout of the base wall 210 from the channel 155 in a direction transversely to the channel length. A preferred configuration of the self-retaining portion is shown in FIG. 7 in the form of the aforementioned tab/barb 250 also termed self-retaining clip. One or more of the tabs/barbs 250 may be used. These tabs/barbs 250, are configured to engage a stabilizer lock portion, shown in the form of undercut regions 125 in spacer 100. Here tabs/barbs 250 are formed on the stabilizer base wall 210 and extend slightly below the base wall 210. As the base wall 210 is inserted into exemplary channel 155, resilient arms 251 on each tab/barb 250 serially engage an edge 139 where deep face 141 bounding the channel 155 meets proximal face 140 and deflects up then re-seats itself under a restoring force when it aligns over an undercut region 125 on the stabilizer interlock. This progression is illustrated in FIGS. 9-11. A portion of the stabilizer body 290 is cut away in the illustrations for enhanced visualization. FIG. 10 illustrates the leading base wall nose 211 approaching one of the channels 155 with the spacer 100 and stabilizer 200 in a pre-assembly relationship. FIG. 11 illustrates stabilizer 200 fully translated into the channel 155 and the spacer 100 and stabilizer in assembled relationship. Stabilizer stop 176 may be positioned at a more proximal on the spacer 100 to prevent further translation of the stabilizer 200 as it moves in its assembly direction. The stabilizer 200 is thus fully locked consistently in a preselected, optimal operative position relative to the spacer/cage 100.

The tabs/barbs 250 may each have a sloped leading surface 253 to assist deflection of the tabs/barbs 250 upon entry and a steeper surface 254 on the trailing end of the tabs/barbs 250 to confront the edges 127 bounding the undercut regions and prevent backout. The transition between the leading surfaces 253 and trailing surfaces 254 may be rounded to prevent hang-ups. The spaces above the tabs/barbs 250 are open to form relief pockets 252 to allow for adequate deflection of the tabs/barbs 250 when inserting into the channel, as described previously. The barb arms 251 are long enough to assure adequate deflection of the barbs 250 while minimizing plastic deformation. The backout stop edges 127 are each in the form of a steep wall located at the trailing end of the undercut regions 125, one of which is adjacent the proximal face 140 with the spacer 100 and stabilizer 200 in operative relationship. The stop edges 127 secure the stabilizer 200 captively in conjunction with the stop portion 176 and help prevent the tabs/barbs 250 from slipping out of the undercut regions 125 as might allow unintended release of the stabilizer 200 from the spacer 100.

With this arrangement, the stabilizer 200 can be translated in a first direction in a first path relative to the spacer/cage 100 and thereby snap-fit consistently into the same operative relationship therewith. The trailing steep surface 254 and edges 127 function as oppositely facing blocking surfaces that confront each other to prevent separation of the operatively joined stabilizer 200 and spacer 100 when the assembly is in an operative relationship.

One preferred interface between flat base wall 210 and channels 155, 165 is the depicted "T"-shaped configuration. Although clearly other shaped channel interfaces can be used, such as triangular, this "T"-shaped interface creates robust stability between the stabilizer 200 and the spacer/cage 100 and in turn results in greater stability of the adjacent bone portions.

Figure 8:
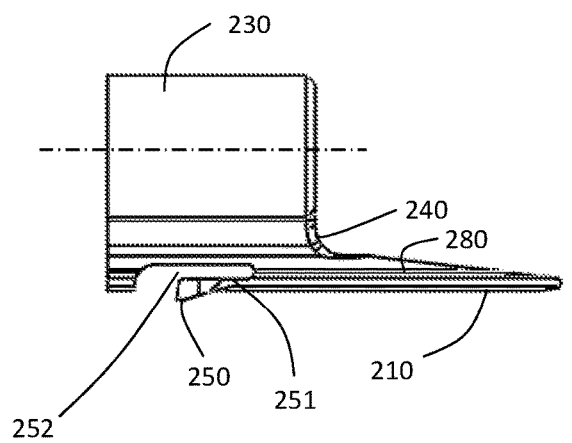
FIG. 8 is a side view of the stabilizer portion of a bone stabilization implant assembly illustrated in FIG. 6.

Web wall 220 is typically in the form of a thin wall, preferably about 1 mm or less, with a sharp leading edge 240 to slice through bone as the stabilizer is advanced in its assembly direction and path, and has a profile narrower than the diameter of the cylindrical wall 230 so the cylindrical wall 230 is captive and cannot be pulled through the bone space created by the web wall 220 thereby securing the bone tightly to the opposite surfaces 110, 120 of spacer/cage 100. Web wall 220 spans along a majority of the length of cylindrical wall 230 but typically less than the length of the flat base wall 210 as illustrated in FIG. 8. It is preferred that the cylindrical wall 230 and web wall 220 and base wall 210 all extend fully to the stabilizer's proximal face 221, and resides in a plane generally orthogonal to the length of the stabilizer 200.

Web edge 240 is preferably sharpened to cut through bone during insertion. This sharpened edge 240 may be vertical or sloped forward or back to facilitate the cutting action. In the preferred embodiment, the web edge 240 is straight, but may also be curved or serrated. It is preferred that the web wall 220 is continuous, but it may include apertures for eventual bone ingrowth. However, these apertures should be limited so as to not substantially weaken the web wall 220. A continuous web will also ease future removal if necessary, since bone cannot grow through the web openings. The web wall 220 in preferred embodiments rises vertically from the flat wall track (base wall) 210; however, the web may rise at an angle or in a curved path if so desired. Retaining member 230 may also include apertures for bone growth if so desired.

Cylindrical wall 230 in this preferred embodiment (FIG. 6-8) is a portion of the stabilizer 200 that is configured with a boundary surface 203 that faces base wall surface 280 to prevent the stabilizer from being pulled through bone as the cooperating bone portion attempts to pull away from the spacer 100 during normal movements of the patient. For purposes of the description and claims herein, the surfaces 203, 280 are considered to be "facing" over the extent to which they are cooperatively capable of exerting a captive force on components therebetween. Essentially, convex surface 203 faces base wall surface 280 at all locations where the surface 203 faces the plane within which surface 280 resides. The cylindrical shape of the wall 230 affords a substantial bone contact area and thus improves overall stability without occupying a detrimentally large bone volume. Surface 280 does not have to be formed as part of a continuous cylindrical surface as depicted, but is preferably convex where it faces the base wall surface 280. The convex portion preferably has a radius at or adjacent the lengthwise central axis-A shown for the cylindrical wall 230. The cylindrical wall 230 may alternatively be an enlarged portion of the implant such as an elongated bulb or cylinder and is configured to prevent pullout from the vertebrae like the "T" shaped walls of the stabilizer spacer anchor 270 prevent pullout from the channels 155, 165. The cylindrical shape of the cylindrical wall 230 is well suited to occupy the space created by a drilled hole in the body of the vertebrae. This is advantageous since drills are one of the tools of choice for orthopedic surgeons since they perform well in narrow spaces, are easy to control, and can be used to form bores quickly. The cylindrical bore produced by drilling also is desirable from the standpoint of avoiding crack propagation. The continuously curved surface produced by boring does not have sharp corners or intersections at which there may be stress concentration.

In alternative embodiments, shapes other than a cylindrical for the wall retaining member 230 is contemplated. Other shapes, derivable by those skilled in the art, may be utilized to prevent the wall/retaining member from pulling through the bone. For example, a "T"-shaped component could be utilized and has a more compact shape. Further, a convex surface may be formed without a full cylindrical shape. In preferred embodiments, the cylindrical wall is continuous defining a fully enclosed central bore 231, however in alternative embodiments the cylindrical wall may be partially open.

Stabilizer cylindrical wall 230 preferably has a reduced lead-in portion to ease insertion of the stabilizer 100 into the bone. This is illustrated in FIGS. 7-8 in the form of a lead 261 having a tapered surface portion angled between a leading end 262 and the surface 203. As the stabilizer 200 is advanced in its assembly path in the assembly direction, the lead 261 bears against the bone portion into which it is directed and progressively wedges that bone portion towards spacer 100.

Figure 6:
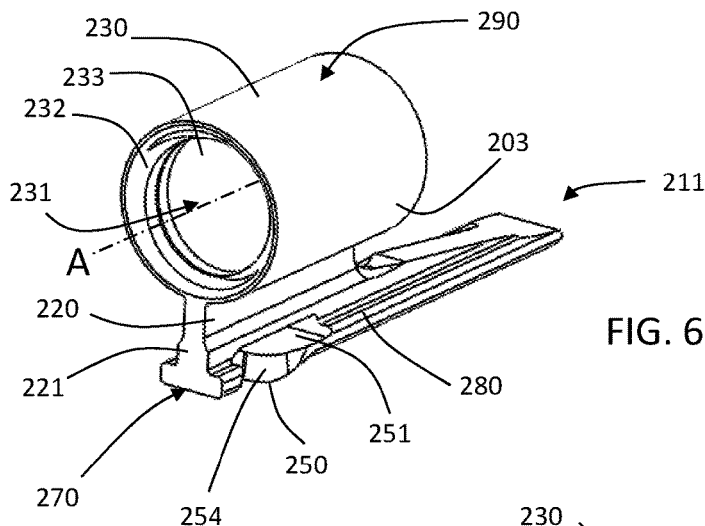
FIG. 6 is a top perspective view of a preferred embodiment of a stabilizer portion of a bone stabilization implant assembly.

The cylindrical wall of stabilizer retaining member 230 has a central bore 231 (FIG. 6). The bore 231 has a central axis A and is defined by bore surface 233. A portion of this bore, preferably at the trailing end, has threads 232 or other functional form of screw anti-backout mechanism to securely contain a stabilizer screw 800 (FIG. 2, 11) within the central bore 231. The stabilizer screw 800, sometimes referred to as a stabilizer anchor, has a diameter to occupy the central bore 231 so that it will be guided in sliding movement therewithin along the axis A.

Figure 12:
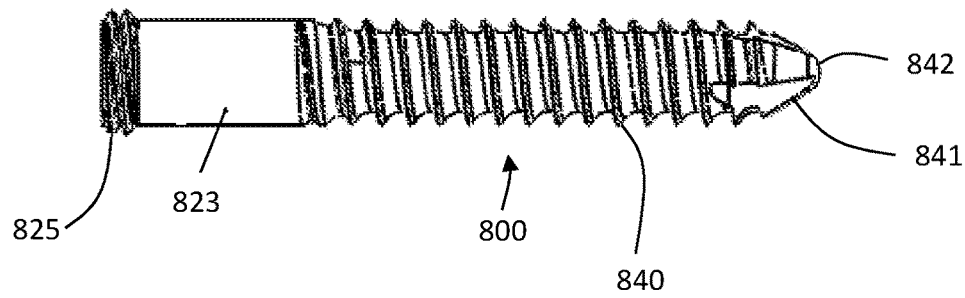
FIG. 12 is a side view of a preferred embodiment of a stabilizer anchor.
Figure 13:
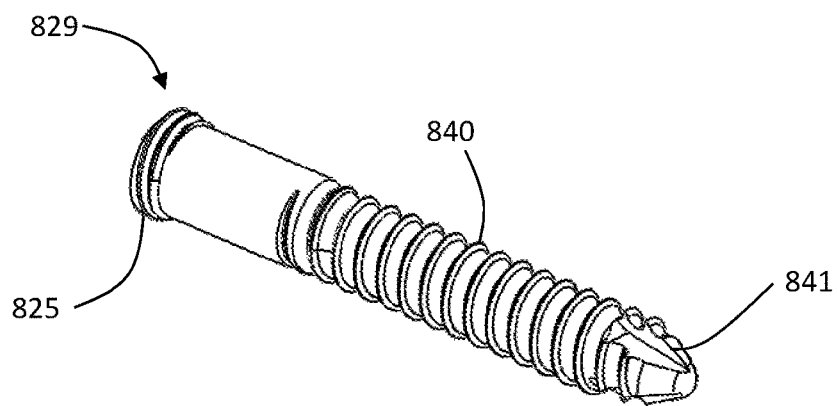
FIG. 13 is a top perspective view of a preferred embodiment of a stabilizer anchor.
Figure 14:
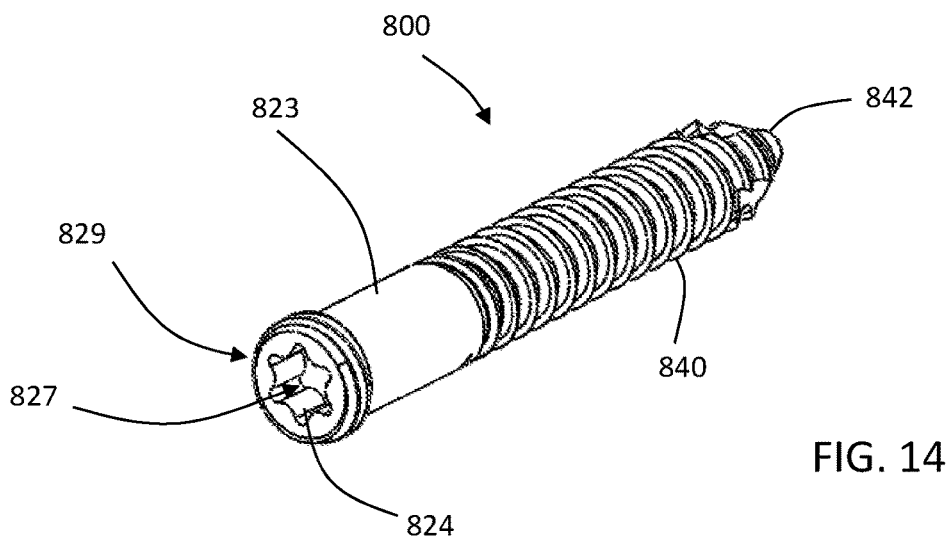
FIG. 14 is a different top perspective view of a preferred embodiment of a stabilizer anchor.

A preferred embodiment of a stabilizer anchor 800 is illustrated in FIGS. 12-14. Stabilizer anchor 800 comprises a shank portion bounded by a shaft face 823 sized for sliding fit within central bore 231. The shaft face 823 may be smooth or may comprise a continuation of the bone screw threads 840 disposed on a distal portion of screw 800. Bone screw threads 840 may assume a variety of forms. In preferred embodiments threads 840 are optimized for seating within cancellous bone. The thread form will preferably include a substantially upright proximal face and a more sloped distal face for eased insertion while demonstrating improved pullout strength. A distally located screw tip 842 is preferably rounded but may be sharp. One or more cutting flutes 841 may be used to ease insertion into bone. At the proximal end of the stabilizer screw 800 are lock threads 825 for cooperation with the threads/connection mechanism 232 of stabilizer 200 to assist in prevention of unintended back out of screw 800 once implanted in an operative relationship. The major diameter of lock threads 825 is larger than the diameter of central bore 231. The stabilizer screw 800 is directed through bore 231 and advanced into bone by threaded rotation until lock threads 825 are fully seated in threads 232 of body 290. In preferred embodiments, lock threads 825 at drive head 829 have two starts to minimize binding when advancing screw 800 and lining up threads 825 and 232. The pitch of threads 825 at head of screw 800 is preferably equal to bone screw threads 840. In alternative embodiments, threads 825 and 232 are absent therein eliminating this form of screw anti-backout mechanism.

Located at the proximal or otherwise trailing end of a stabilizer screw 800 is a drive head 829 which in this embodiment comprises a drive pocket 827 with an array of drive faces 824 thereon for the transmission of torsional forces from a drive instrument to stabilizer screw 800. Pocket 827 is configured to receive and intermesh with drive faces 734 on a drive head 733 of a stabilizer screw driver 700 (one embodiment illustrated in FIGS. 15-16) such that turning of a stabilizer screw driver 700 through a hand-graspable driver handle 731 (shown removed from driver 700) or power instrument will advance a stabilizer screw 800 into stabilizer 200 central bore 231 for locking into bone.

Figure 15:
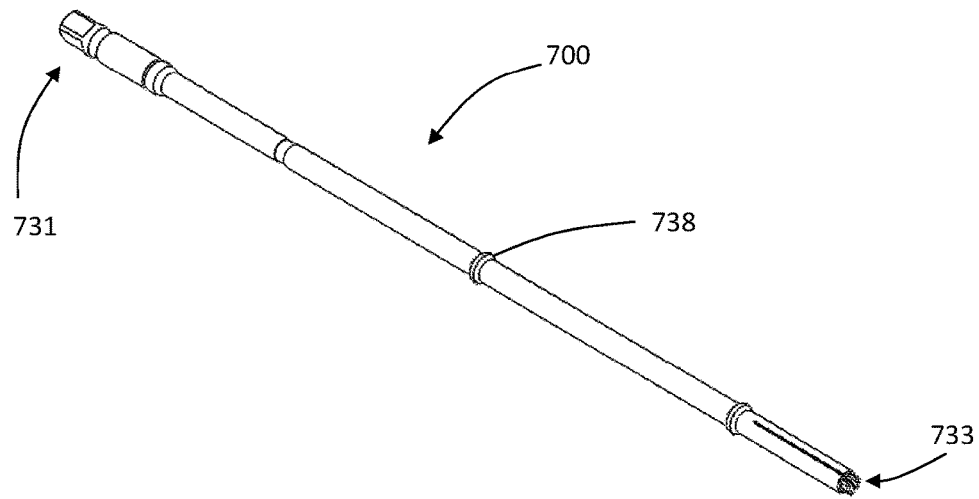
FIG. 15 is a top perspective view of a preferred embodiment of a stabilizer anchor driver.
Figure 16:
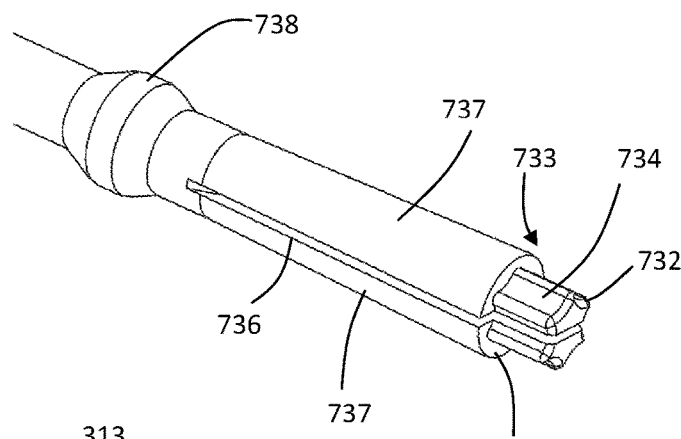
FIG. 16 is a partial close up view of the drive end of the anchor driver illustrated in FIG. 15.

A leading end of the drive head 733 may be configured for eased insertion into drive pocket 827 by using a taper 732, radius, or other means and may also have a shoulder 735 to stop insertion consistently at a preferred depth in drive pocket 827. To prevent unintended separation of stabilizer screw driver 700 from the stabilizer screw 800, drive head 733 may incorporate an anti-separation feature. For example, in this embodiment (FIG. 15-16) drive head 733 may be bifurcated or otherwise split one or more times to create repositionable arms 737 separated by one or more deflection gaps 736. It is preferred that arms 737 elastically spring out to create an outside diameter of drive head 733 that is slightly larger than that of the drive pocket 827 so that, when inserted, a frictional fit of the drive head 733 within the drive pocket 827 is created with the arms 737 wedged towards each other, wherein the stabilizer screw 800 is not prone to unintentionally falling off yet is easily released when needed by the surgeon by intentional retraction of the stabilizer screw driver 700 once stabilizer screw 800 is seated into bone. Stabilizer screw driver 700 may include one or more alignment faces 738 as illustrated in FIG. 15-16 to assist centering in a drill guide cylinder.

Various forms of other instruments usable to install spacer-stabilizer assemblies into the affected intervertebral spaces are described below.

Figure 17:
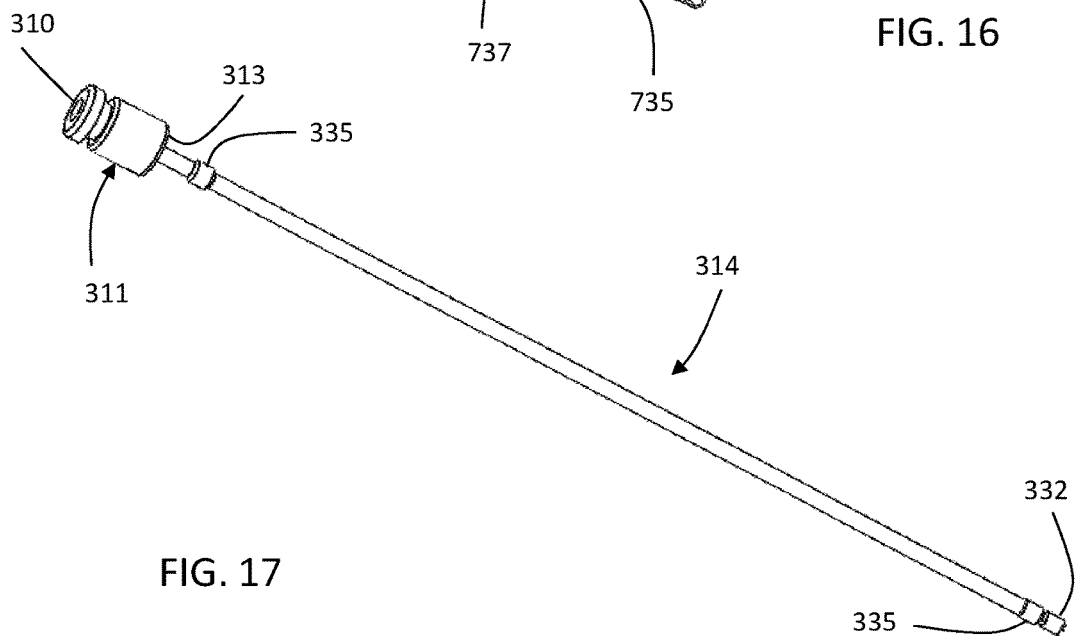
FIG. 17 is a front perspective view of a preferred embodiment of a locking shaft.

In a preferred embodiment of a spacer inserter tool 300, the tool 300 is attached to a spacer body 190 at an instrument attachment portion 108 of a implant spacer/cage 100. The spacer inserter 300 has a connection tip portion 340 at a distal end of a guide bar body 330 which, in this embodiment, the connection tip portion is also in the form of a threaded prong 332 and a non-threaded prong 331 for engagement in the attachment holes of implant body 190 illustrated in FIG. 5 as 115a, 115b. Both of these holes/bores 115a, 115b may be threaded for reasons stated earlier although one may be unthreaded. The non-threaded prong 331 resides in the one of the instrument attachment bores 115a, 115b of an implant spacer/cage 100 that may be unthreaded. The threaded prong 332 threads into the remaining threaded hole 115a, 115b and holds the implant spacer/cage 100 tight to an inserter face 333. Together, both prongs 331, 332 serve to maintain consistent alignment of the spacer inserter instrument 300 with the implant body 190 thereby controlling the implant spacer 100 during insertion. In this embodiment, threaded prong 332 is the distal portion of locking shaft 314 as illustrated in FIG. 17.

The connection tip 340 portion may take other forms such as a bayonet connection or clamping arms or non-circular boss end. The instrument attachment portion 108 is then configured with a structure complementary to these other forms to impart control on the spacer 100.

Figure 20:
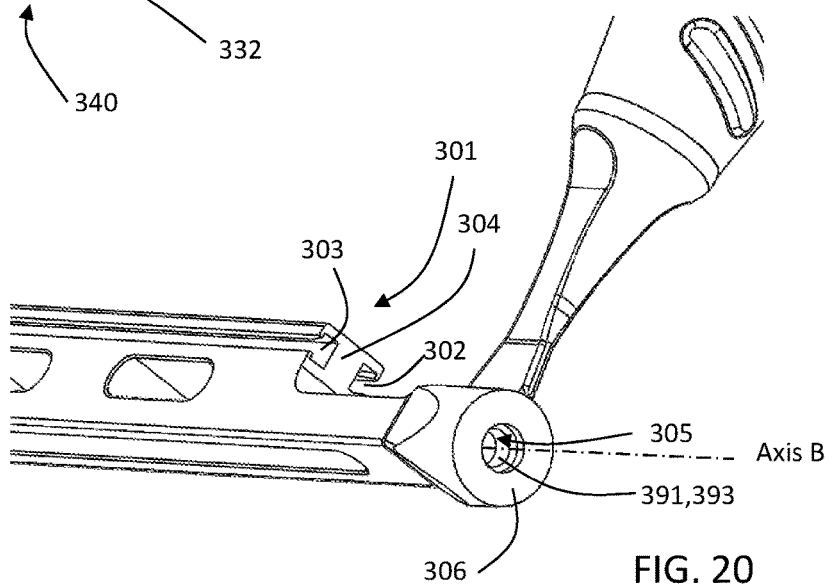
FIG. 20 is a partial close up view of the proximal end of the spacer inserter illustrated in FIG. 18.

The guide bar body 330 may include a handle portion 320 for user control over the inserter tool 300. This handle 320 has a graspable length that is preferably oriented to be angled, in one form on the order of 90 degrees to the central axis-B of bar body 330. Guide bar body 330 houses locking shaft 314 (FIG. 17) within a locking shaft aperture 305 as illustrated in FIG. 20. A threading spool 311, sized and shaped for finger advancement, is provided for the user to advance locking shaft 314, which terminates at the threaded prong 332 as illustrated in FIG. 17 (threads not shown). One or more alignment faces 335 may reside on locking shaft 314 for alignment within the guide bar body 330. As the threading spool 311 is hand rotated, the threaded prong 332 seats into one of the threaded attachment holes 115a, 115b on the implant, therein securing the implant spacer/cage 100 to the inserter tool 300. The non-threaded prong 331 seats in the remaining attachment hole to prevent rotation of the implant relative to the guide bar body.

A handle 320 and guide bar body 330 may be used by the surgeon to control insertion of a spacer/cage 100 into an intervertebral space. A nose 101 of the implant spacer/cage 100 is guided into a predetermined position between the vertebral endplates. An impact fitting 310 on the proximal end of locking shaft 314 may be tapped with a hammer to assist driving the implant spacer/cage 100 into the intervertebral space. This impact force is transmitted from a transmission face 313 of locking shaft 314 to the adjacent transmission face 306 of a guide bar body 330 then through inserter face 333 to the spacer proximal face 140.

A guide bar body 330 may have one or more access apertures 334 along the length of body 330 to facilitate viewing and/or cleaning. The length of the guide bar body 330 is preferred to be of sufficient length wherein an attached handle 320 can be grasped a comfortable distance outside of an incision above a patient's skin. Distal portions of inserter tool 300 are sized to freely pass through an internal channel formed by a tissue retractor or surgical tube.

Figure 18:
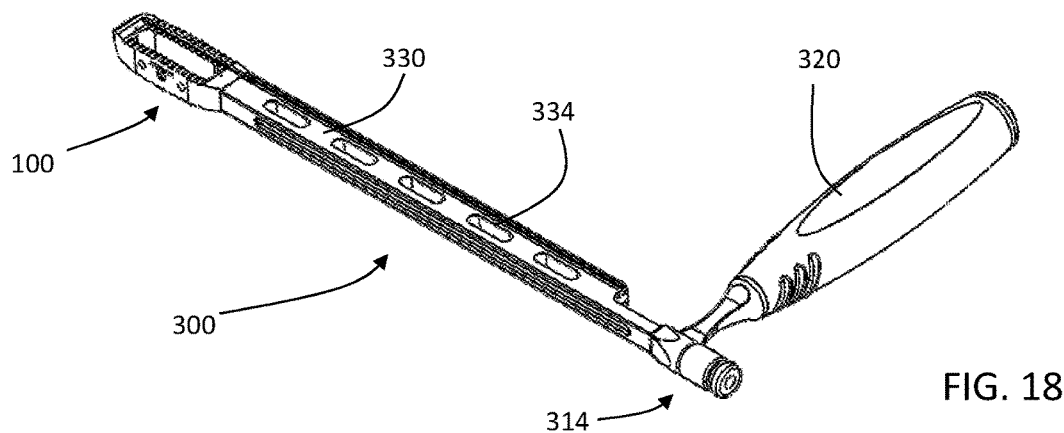
FIG. 18 is a top perspective view of a preferred embodiment of a spacer and spacer inserter assembly.
Figure 19:
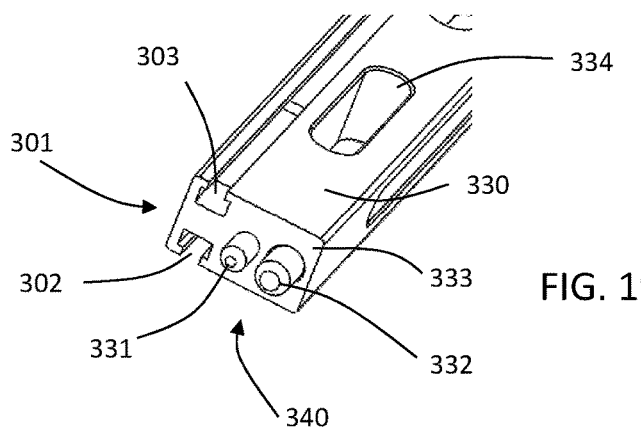
FIG. 19 is a partial close up view of the distal end of the spacer inserter illustrated in FIG. 18.

The guide bar body 330 illustrated in assembly in FIG. 18, includes a longitudinal guide 301 illustrated in FIG. 19-20 in the form of opposing T-shaped channels 302 and 303. The T-shaped channels 302, 303 are defined by guide walls with guide surfaces on each guide wall. The profile of the T-shape may vary in width along the length of the channel and entry into the channels from a proximal or distal end may be sloped to provide eased entry into or out of the channel by other implant or instrument parts. Channels 302 and 303 are preferably configured of similar profile and dimension and align with spacer channels 155 and 165 when inserter 300 is secured to spacer 100 as illustrated in FIG. 18. Like spacer channels 155 and 165, it is preferred channels 302 and 303 are configured to capture implant components and instruments for linear sliding engagement down guide bar body 330 and into spacer channels 155 and 165 to assure alignment of additional implants and instruments with the spacer and bone portions. For example, spacer anchor 270 portion (FIG. 6) of stabilizer 200 may be inserted at proximal channel face 304 of inserter 300 into channels 302 and 303. In this configuration, stabilizer 200 and instruments such as drill guides are guided from the entrance of the incision down to their pre-determined location within the patient's body therein avoiding the challenges of aligning these structures deeper within the incision site when surgical vision is compromised by surrounding tissue. At the proximal end of a inserter body 330 is inserter transmission face 306 positioned to transfer impact forces applied by a hammer to impact fitting 310 of locking shaft 314, as well as fixation forces by transmission face 313 of locking shaft 314 when locking spacer 100 to inserter 300. An elongated locking shaft aperture 305 extends the length of guide bar body 330 along axis-B and is sized to house locking shaft 314 therein. The shaft aperture 305 is defined by shaft aperture walls 391 and shaft aperture surface 393 situated on these walls.

Figure 29:
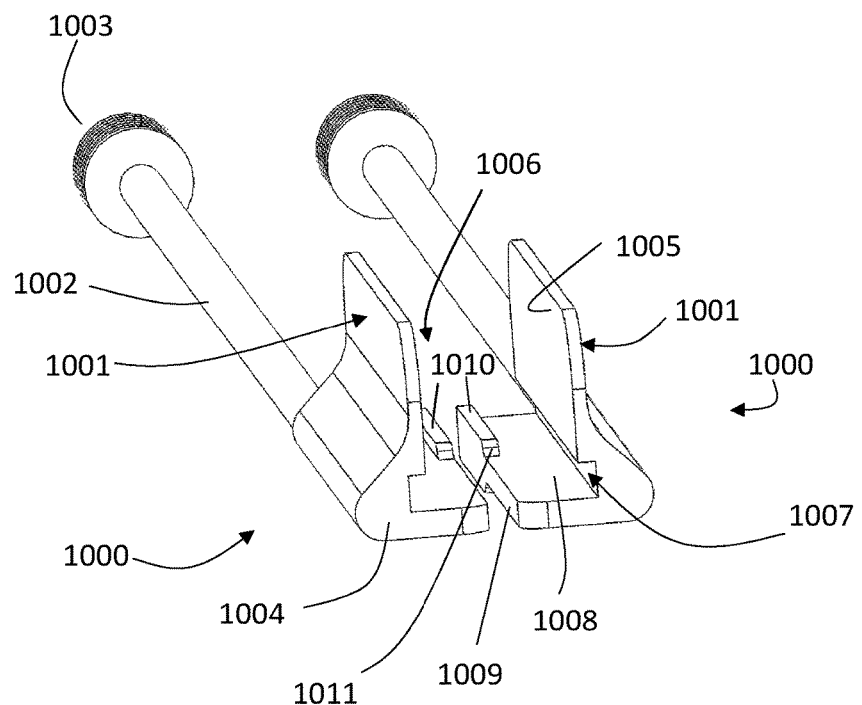
FIG. 29 is a distal perspective view of a preferred embodiment of a pair of graft blocks.
Figure 30:
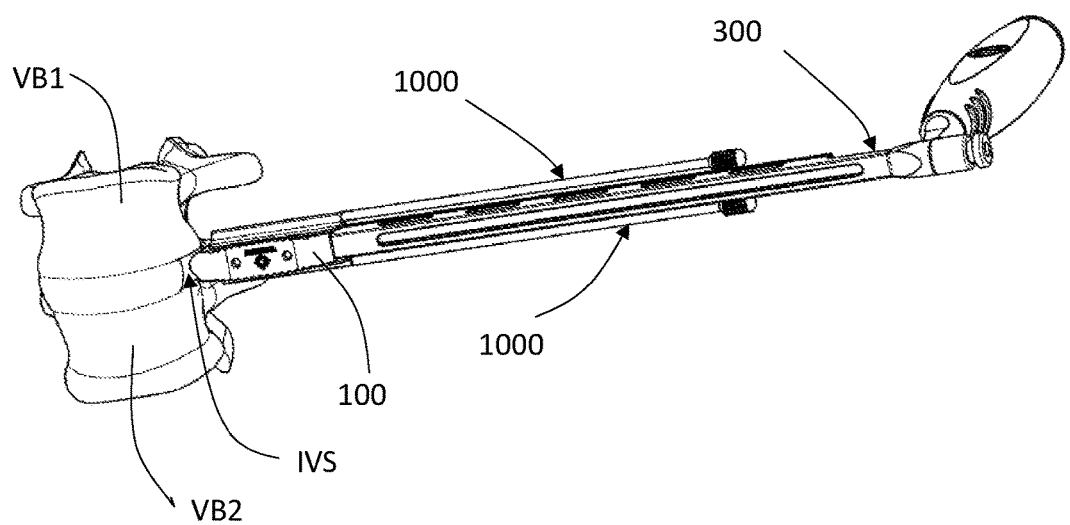
FIG. 30 is an anterior perspective view of a preferred embodiment of a spacer being inserted into a vertebral space IVS between two vertebral bodies VB1 and VB2.

Illustrated in FIGS. 29-30 are additional exemplary instruments configured for use with inserter tool 300. One or more graft blocks 1000 may be utilized to secure bone graft or other bone substitutes within opening 132 of spacer 100 during insertion of a spacer into a predetermined surgical space. In this embodiment, graft blocks 1000 are paired and may be generally mirror images of each other. Each graft block 1000 is configured to enclose a graft opening 132 of a spacer 100 and therefore a paddle portion 1001 of the graft block 1000 may assume other shapes as required for this function. In this embodiment graft block 1000 are in the form of generally rectangular shaped paddle 1001 with containing face 1005 facing opening 132 of spacer 100. Paddle arm 1002 extends from paddle 1001 and terminates in paddle handle 1003 for grasping by surgeon. A handle portion may be enlarged and may be knurled or include other textures or coverings to improve grip. At a distal end of paddle 1001 is stop face 1004 for abutting bone or other mechanical stops. One or more channel locks 1006 align a graft block within an inserter tool 300 and spacer 100. In this embodiment, the channel locks 1006 are in the form of opposing alignment bosses 1010 shaped for capture and sliding engagement within channels 302 or 303 of longitudinal guide 301. Although channel lock 1006 is illustrated here in the form of a T-shaped complementary engagement, other shapes and forms may be assumed to complement profiles in the instrument. Channel lock 1006 may include a butt face 1011 to abut against a stop on a spacer to indicate proper paddle alignment over the graft apertures.

Relief groove 1007 may be provided to assist sliding of paddles 1001 along guide bar body 330 and to provide deflection of paddle 1001 to accommodate various sizes of spacers 100. Spacing wall 1008 distances paddle 1001 a predetermined distance from axis-B of inserter tool 300 sufficiently for paddle to cover graft opening 132. Bottom paddle surface 1009 glides along bottom surface of channel 302 or 303.

Figure 24:
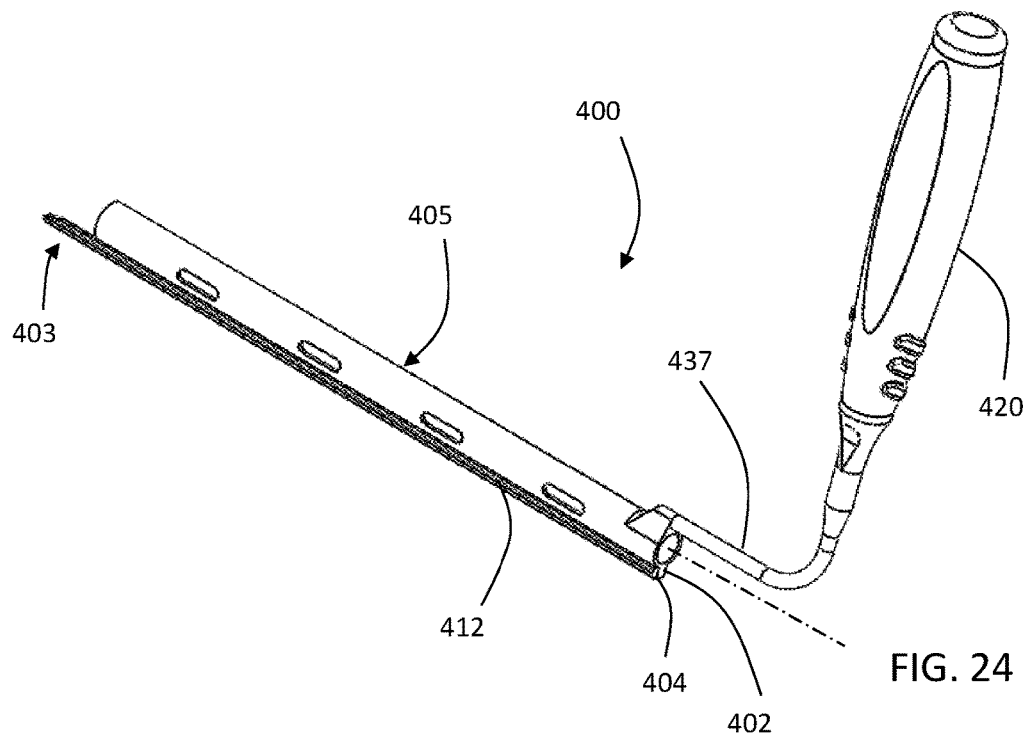
FIG. 24 is a side perspective view of a preferred embodiment of a drill guide.
Figure 25:
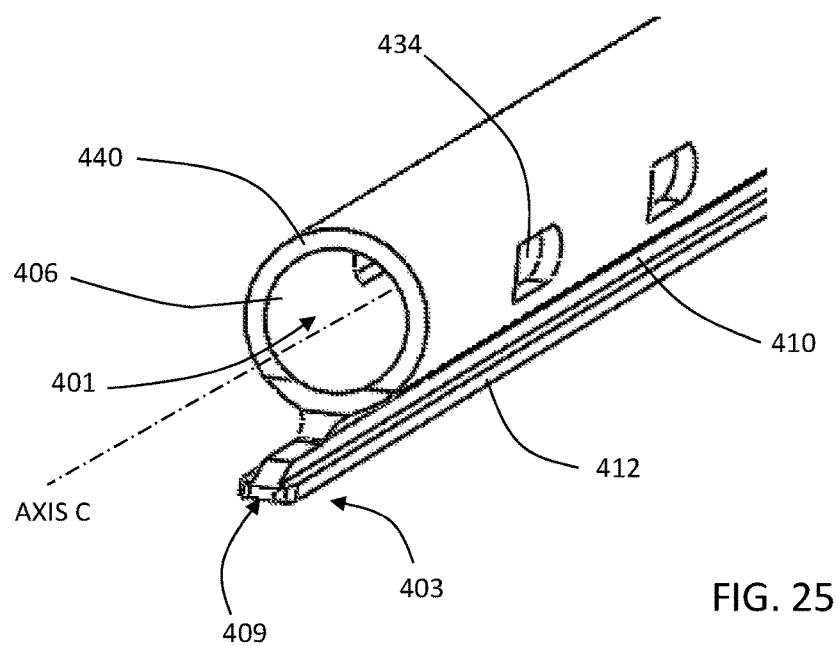
FIG. 25 is a partial close up view of a base nose of the drill guide illustrated in FIG. 24.

Illustrated in FIGS. 24-25 is drill guide 400 configured for compatibility with inserter 300 wherein drill guide 400 is configured for engagement in channels 302,303 of spacer inserter 300. During portions of surgery, drill guide 400 is interconnected with the longitudinal guide 301 of the spacer inserter tool 300. This relationship assures the drill guide 400 is held stable in the incision and accurately positioned on a predetermined bone portion site for drilling of a stabilizer hole that will later be occupied by a stabilizer 200.

Drill guide body 405 spans between a drill guide tip 403 and a drill guide shoulder 402. The drill guide body 405 has a drill guide wall 406, the face of which in this case defines a drill guide cylinder 401 to receive and guide a drill 500 such as shown in FIG. 21-23. Although the wall 406 is illustrated as a continuous cylinder, the wall 406 may be discontinuous. For example, the wall 406 may be in the form of a plurality of tabs extending from the drill guide body 405 yet still functioning to contain and guide a drill 500. Preferably at the proximal end of the drill guide body 405, although it could be positioned elsewhere, a drill guide shoulder 402 is provided. This shoulder 402 interfaces with a drill guide stop 522 on a drill 500 to stop penetration of the drill 500 into the bone at a predetermined depth. The drill exits the distal cylinder face 440 before proceeding to engage a bone portion such as a vertebral body.

Tip 403 (FIG. 24-25) of this embodiment is distally located on drill guide body 405. Tip 403 is configured in profile and size to fit within complementary inserter channels 302 and 303 as well as spacer channels 155, 165. Drill guide tip 403 of drill guide 400 comprises a flat drill guide track or also termed a drill guide base wall 412, a drill guide web wall 410, and a drill guide base nose 409. The base nose 409 may be one or more of tapered and radiused much like the stabilizer nose 211 to simplify insertion into one of the channels 302, 303. Web wall 410 extends upright from base wall 412 and is integrated into, or otherwise attached to, drill guide body 405. In this embodiment, although not necessary, web wall 410 extends substantially the entire length of guide body 405 parallel to axis-C. A drill guide stop 404 is located near the proximal end of drill guide body 405 at web wall 410 and is in the form of a ridge extending out from the web wall 410. Drill guide stop 404 limits over insertion of a drill guide once the stop 404 abuts a proximal channel surface 304. A drill guide handle assembly extends from a proximal end of drill guide body 405. The handle assembly may include a handle extension 437 for extending a handle portion further proximal from the drill guide body. A drill guide handle extends transversely from handle extension 437 thereby providing a user to control both the position and counter act torsional forces on the drill guide during use. Drill guide body 405 may include one or more drill guide apertures to cleanse the instrument.

In a preferred embodiment, a bone drill is illustrated in FIG. 21-23. Drill 500 has an elongate drill body 529 with central axis F and with several features thereon. A proximal end of drill 500 has a drive shaft 528 with one or more drive faces 523 thereon defining a polygonal outer drive surface. Drive faces 523 are configured to be directed into a complementary shaped receptacle of a removable handle or powered drill 511. Alternatively, the drive shaft could be configured in the shape of a drill handle. Drill stop 522 is configured in this case to abut the drill guide shoulder 402 when a drill 500 has reached its predetermined depth. Drill guide body 529 may also include one or more radially enlarged, cylindrical alignment faces. This embodiment has a proximal alignment face 526 and a distal alignment face 527. When the drill body 529 is situated within drill guide wall 406, these alignment faces 526, 527 are sized to have a diameter slightly less than the inner diameter of the drill guide cylinder 401 to maintain alignment and minimize wobble of the drill 500 during use. A base region 525 is a recessed area on the body which may be configured to separate the alignment faces 526, 527 and for collection of bone chips as the drill 500 engages with and removes bone. In some embodiments, a collection recess 531 may be directly adjacent cutting flutes 524A and 524B as shown in FIG. 22. At the distal end of drill 500 is a cutting tip 521 which is preferably tapered back to engage the bone from a starting point. Cutting flutes 524A extend back helically from the tip 521 to carry bone chips away from the cutting tip 521. The flutes and tip 521 have sharp cutting faces 530 on edges thereon to ease cutting through bone. In this embodiment, drill 500 is of a two-step variety configured for boring two holes of a specified diameter and depth simultaneously. The first step 540A of drill 500 is suited for predrilling a hole to a predetermined depth in the bone the general diameter of the minor diameter of stabilizer anchor 800. The second step 540B of drill 500 is suited for predrilling a hole to a predetermined depth in the bone generally the diameter of the outer diameter of locking sleeve 291 of stabilizer 200.

The surgical instruments as illustrated are well suited for a lateral approach of the spine but may be adapted for other surgical approaches. Many adjustments which fall within the scope of this disclosure may be made to the implants and instruments to accommodate for these other surgical approaches.

An example of a surgical technique for a lateral approach is described below. Adjustments to the surgical technique within the scope of this disclosure are contemplated for other surgical approaches. The surgical method of use begins by preparing the patient using standard pre-op procedures and positioning the patient on an operating table laying with the lateral entry side facing superiorly. EMG monitoring may be used to steer away from nerves. Incisions from the lateral side to open access to the surgical site are made. Tissue dilators and/or retractor systems may be used to access the affected disc space along with access lighting. Diseased disc material is removed and endplates are prepared.

Figure 31:
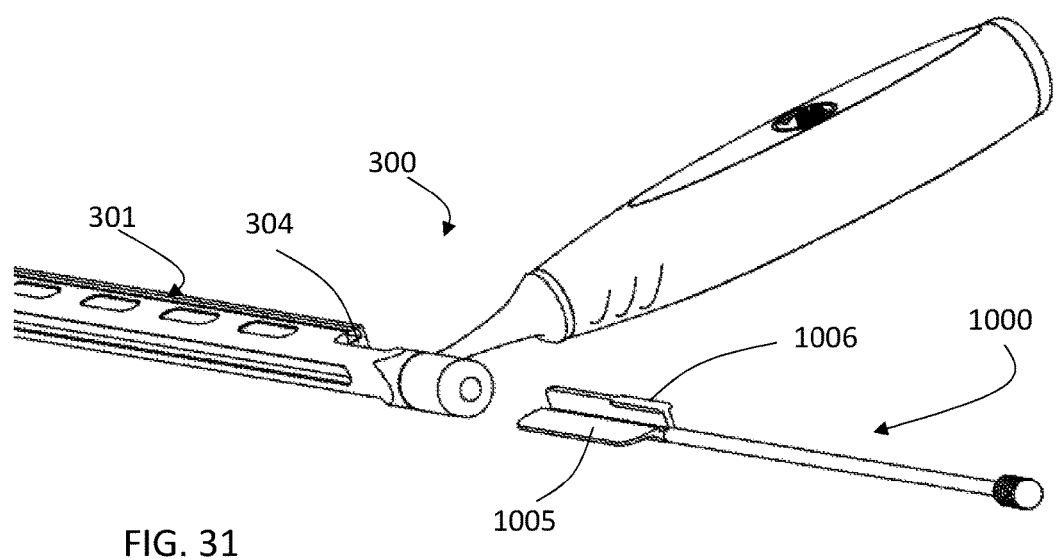
FIG. 31 is a partial top perspective view illustrating one step of a method of inserting a spacer and stabilizer whereby a graft block is about to be inserted into a spacer inserter.
Figure 32:
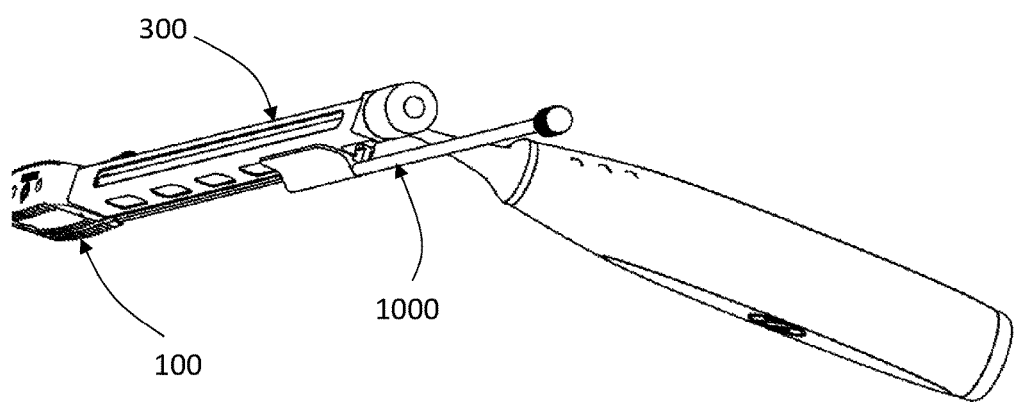
FIG. 32 is a partial proximal perspective view illustrating one step of a method of inserting a spacer and stabilizer whereby a graft block is translated down a longitudinal guide.
Figure 33:
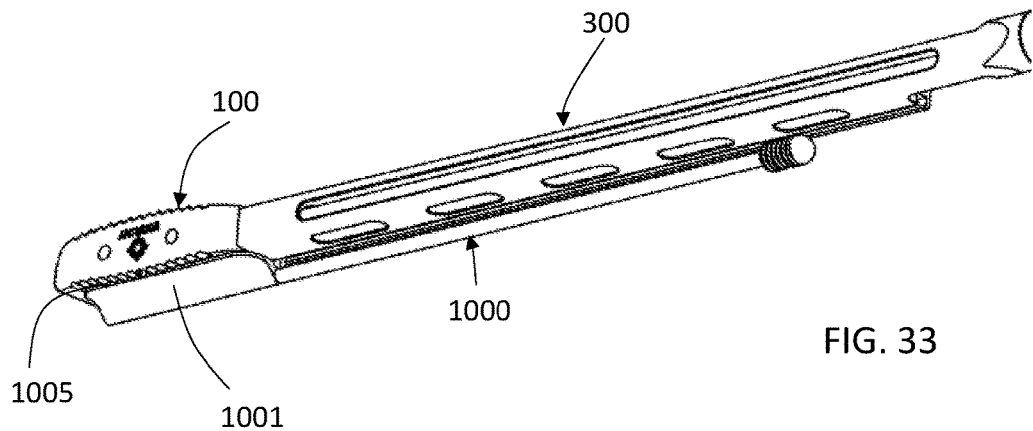
FIG. 33 is a partial side perspective view illustrating one step of a method of inserting a spacer and stabilizer whereby a paddle encloses one side of a graft opening.

Trial spacers, such as the one illustrated in FIG. 26 from the prior art may be used to correctly size the spacer and stabilizer required for the patient. When needed, extension handles may be serially attached to increase handle extension length. The selected spacer corresponding to the size of the intervertebral space is chosen from a surgical kit and secured to spacer inserter tool 300 by advancing locking shaft 302 as previously described. A graft block 1000 is chosen (FIG. 29), and with stop face 1004 facing distal, channel locks 1006 are inserted at the proximal channel surface 304 (FIG. 31) of inserter 300 into the appropriate T-shaped channel 302 or 303 and advanced distally (FIG. 32) until containing face 1005 covers spacer graft opening 132 as illustrated in FIG. 33. Interference between alignment bosses 1010 on the graft block and portions of the inserter or spacer are utilized in some embodiments to stop the graft block at a predetermined position over the graft opening.

Figure 34:
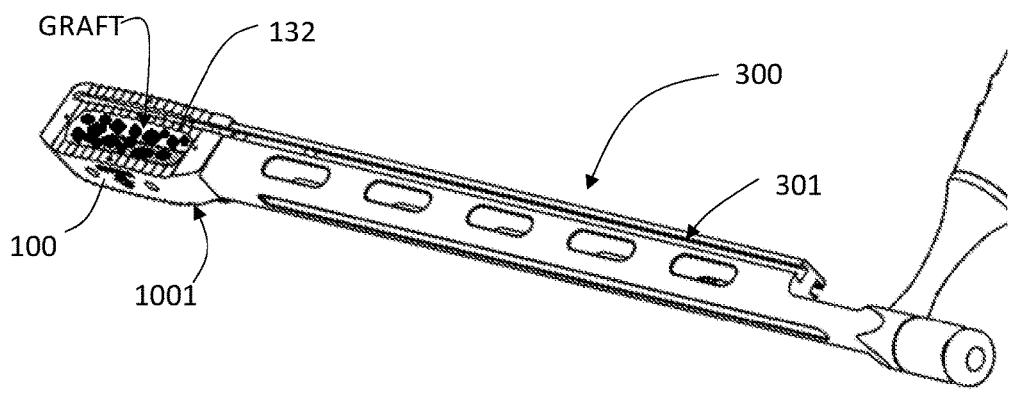
FIG. 34 is a partial top perspective view illustrating one step of a method of inserting a spacer and stabilizer whereby a graft opening in a spacer is filled with graft material.

Holding the assembly so the unblocked spacer opening 132 is facing up so that gravity can assist, the spacer opening 132 may be packed with a chosen graft material as illustrated in FIG. 34.

Figure 35:
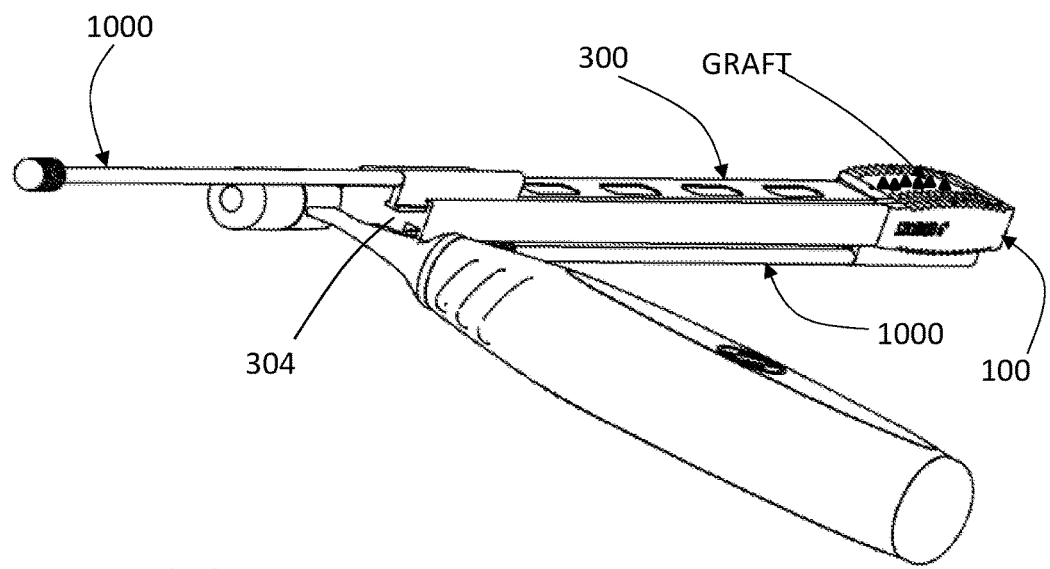
FIG. 35 is a top perspective view illustrating one step of a method of inserting a spacer and stabilizer whereby a second graft block begins to slide down a longitudinal guide.
Figure 36:
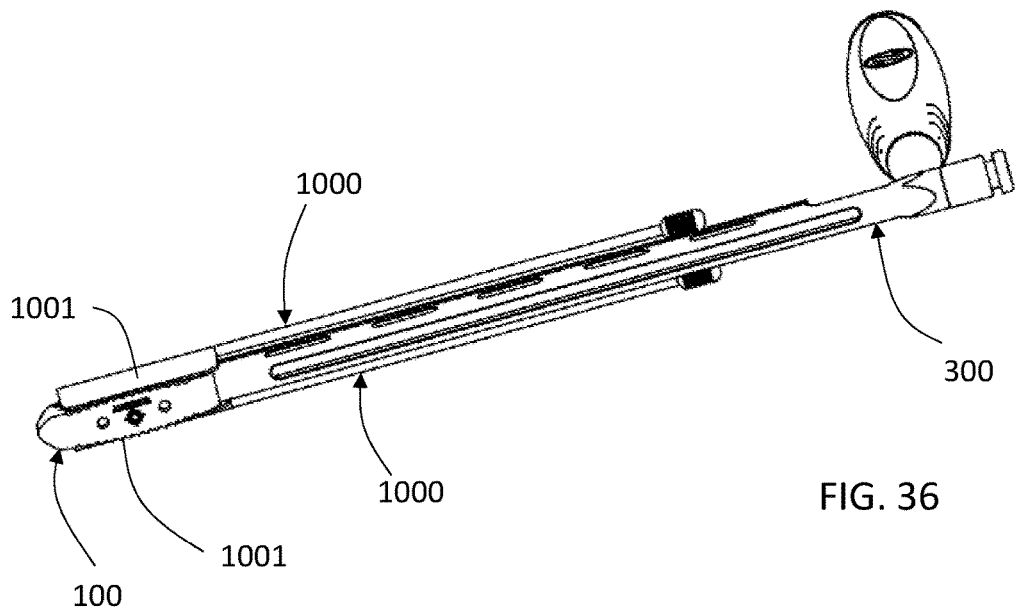
FIG. 36 is a side perspective view illustrating one step of a method of inserting a spacer and stabilizer whereby the graft opening of a spacer is fully enclosed by graft blocks.

If the surgeon chooses, a second graft block 1000 is chosen (FIG. 35) with channel locks 1006 again inserted at proximal channel surface 304 of inserter 300 into an available channel 302 or 303, and advanced distally wherein containing face 1005 covers spacer opening 132. The graft should now be contained by the walls of spacer 100 and each graft block containing face 1005 as illustrated in FIG. 36.

Figure 37:
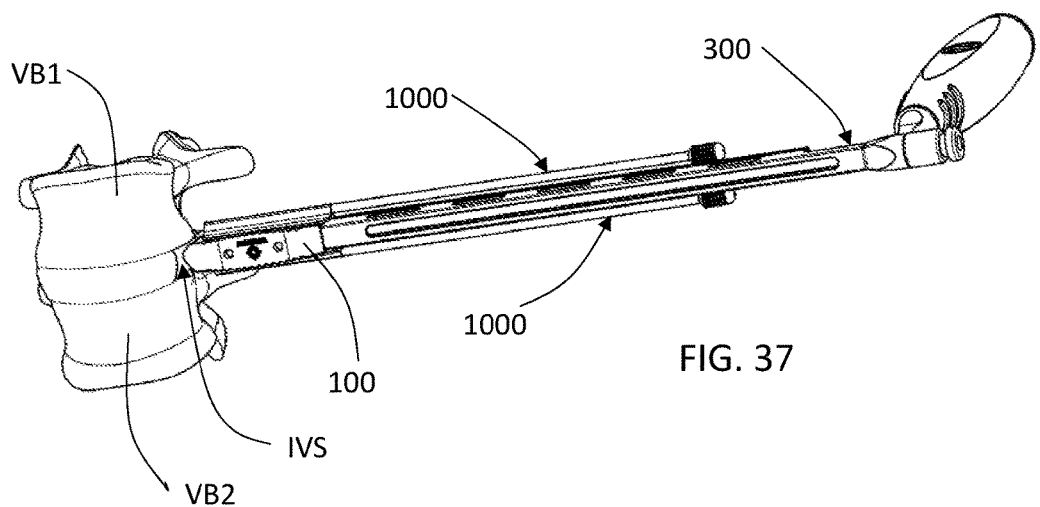
FIG. 37 is a side perspective view illustrating one step of a method of inserting a spacer and stabilizer whereby a spacer is translated towards an intervertebral space.
Figure 38:
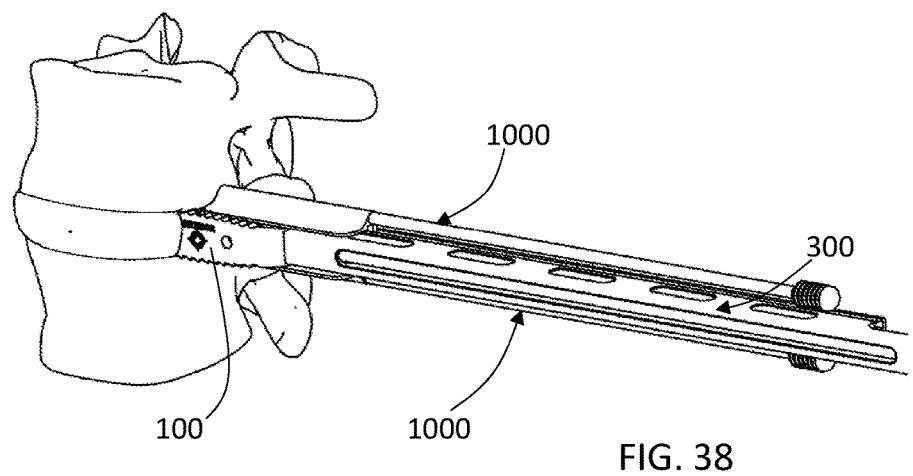
FIG. 38 is a partial side perspective view illustrating one step of a method of inserting a spacer and stabilizer whereby a spacer is partially inserted into an intervertebral space.
Figure 39:
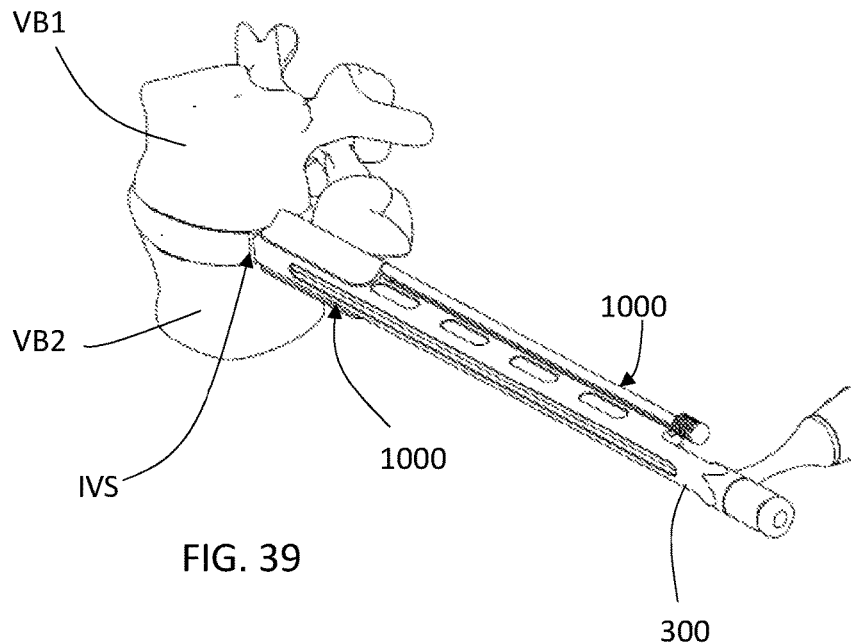
FIG. 39 is a partial top perspective view illustrating one step of a method of inserting a spacer and stabilizer whereby a spacer is fully inserted into an intervertebral space and graft blocks retract as they encounter bone.
Figure 40:
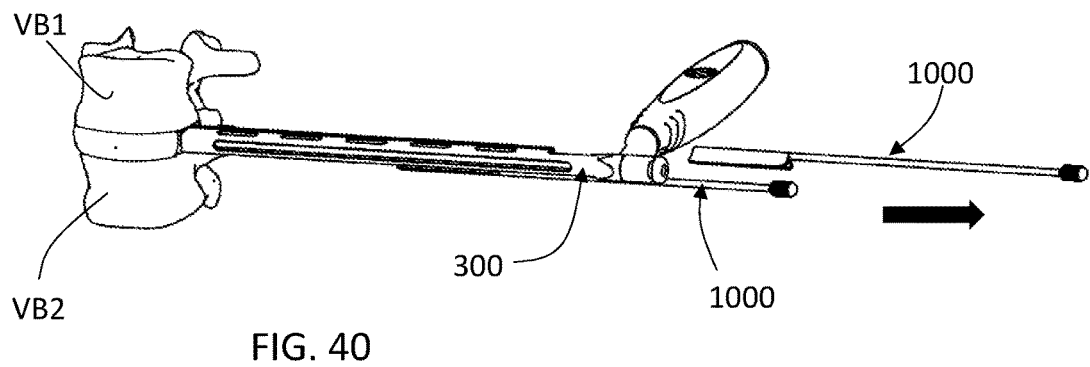
FIG. 40 is a side perspective view illustrating one step of a method of inserting a spacer and stabilizer whereby a pair of graft blocks are removed.

An inserter tool with the selected spacer attached is then guided through the incision, down the corridor created by a retractor, with the leading end of the spacer wedging between the vertebral endplates and stop face 1004 of graft block 1000 abutting a cortical bone wall of vertebral bodies VB1, VB2 (FIG. 37). As spacer 100 is advanced in the intervertebral space IVS, graft blocks 1000 are forced proximally (FIG. 38) until spacer 100 has reached its predetermined position in the intervertebral space (FIG. 39). The graft blocks 1000 may now be removed from the surgical corridor by retracting them proximally (FIG. 40).

Figure 41:
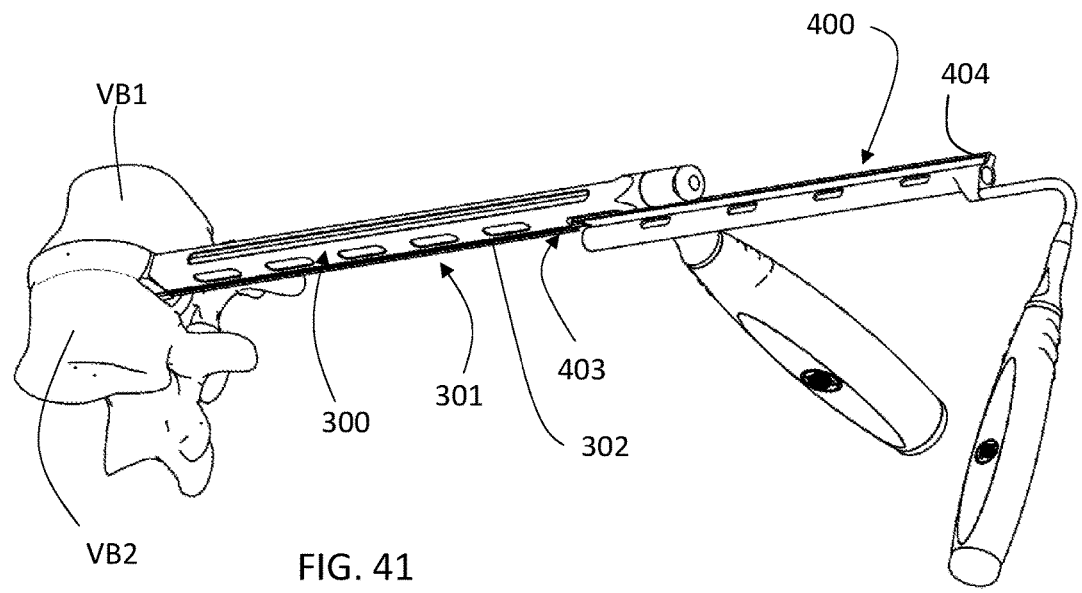
FIG. 41 is a bottom perspective view illustrating one step of a method of inserting a spacer and stabilizer whereby a drill guide is inserted into a longitudinal guide.
Figure 42:
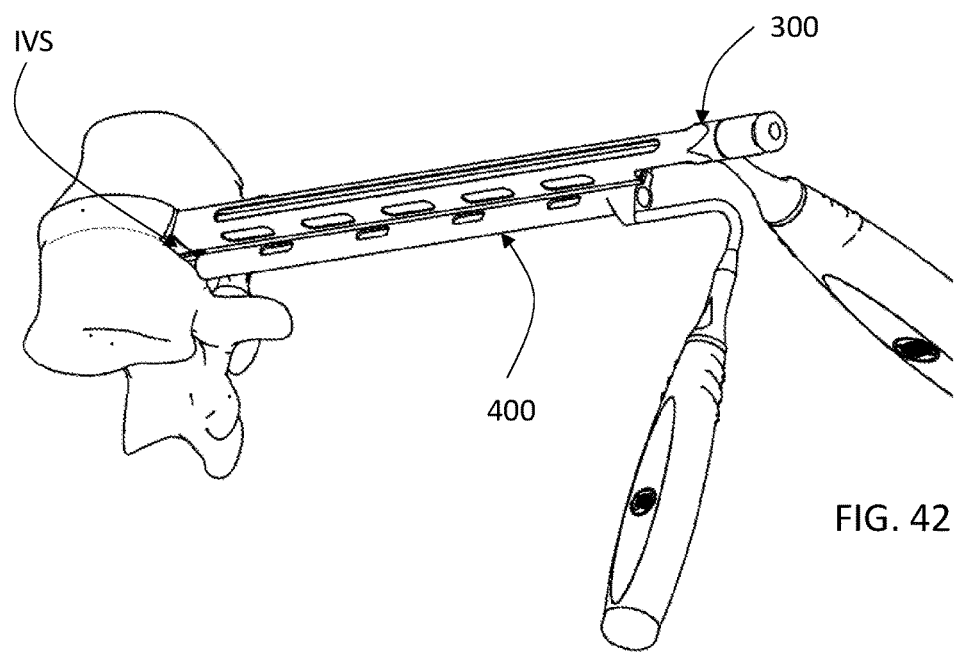
FIG. 42 is a partial bottom perspective view illustrating one step of a method of inserting a spacer and stabilizer whereby a drill guide a fully translated along a longitudinal guide of a spacer inserter.

Tip 403 of drill guide 400 is then inserted into one of channels 302 or 303 (FIG. 41) and advanced distally until proximal channel surface 304 abuts drill guide stop 404. The tip 403 is now engaged within one of the spacer channels/tracks 155, 165 of the spacer/cage 100 assuring correct drill position with respect to the spacer (FIG. 42).

Figure 43:
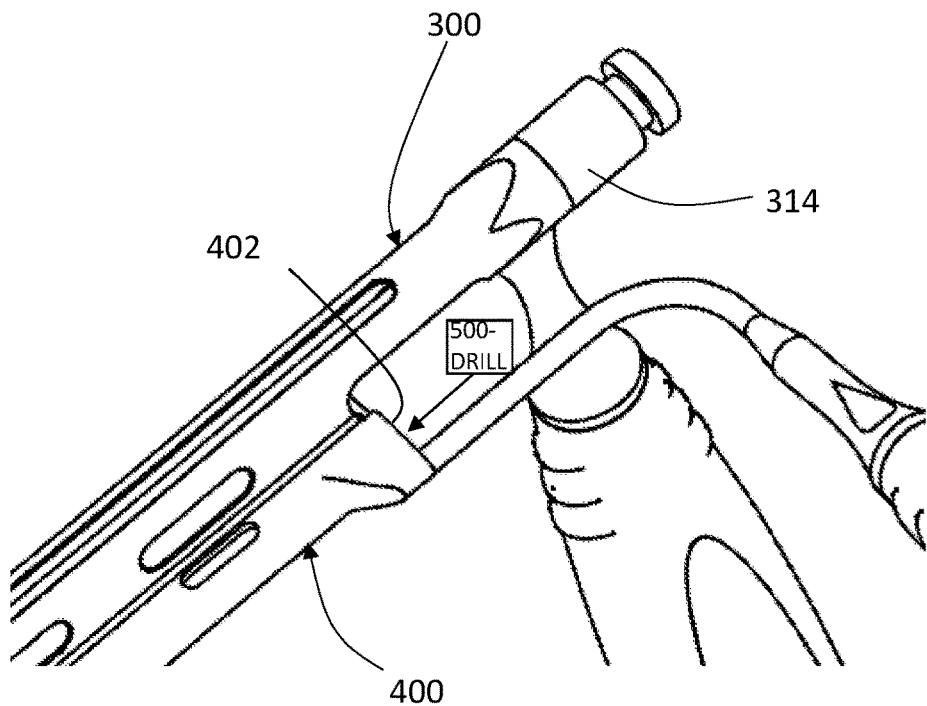
FIG. 43 is a top close up perspective view illustrating one step of a method of inserting a spacer and stabilizer whereby a bone drill is advanced down a drill guide.

A drill 500 (illustrated schematically in FIG. 43) of predetermined diameter for chosen stabilizer 200 and stabilizer anchor 800, is inserted into drill guide cylinder 401 of drill guide 400. A bore is created in the wall of the vertebrae by advancing drill 500 by hand or power into the drill guide cylinder until the drill guide stop 522 abuts drill guide shoulder 402 indicating the drill has reached a pre-determined depth suitable for seating stabilizer 200 and stabilizer anchor 800. A hole having two diameters is created in the bone. The drill 500 and guide 400 are then removed. The procedure is duplicated on the opposing side to create a similar bore. The drill 500 and guide 400 are again removed. (As an alternative, the surgeon may opt to place a stabilizer 200 in position within the 1$^{st}$ drilled hole in the vertebral body before moving on to drill in the opposing vertebrae).

Figure 44:
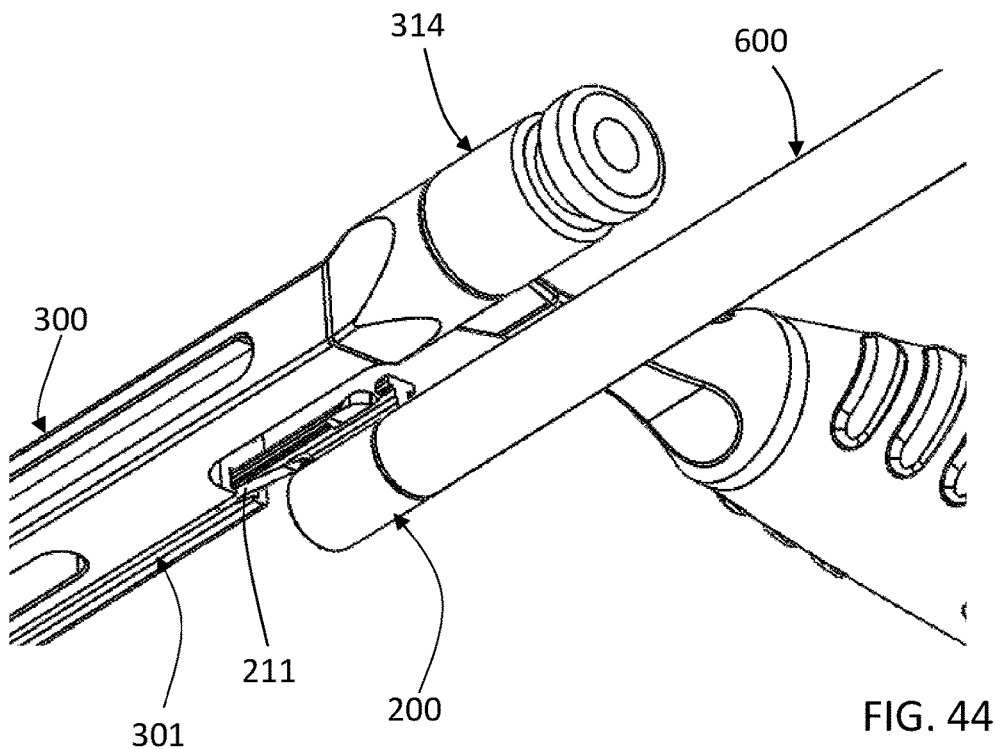
FIG. 44 is a partial top perspective view illustrating one step of a method of inserting a spacer and stabilizer whereby a leading nose of a stabilizer implant portion is inserted into a longitudinal guide of a spacer inserter instrument.
Figure 45:
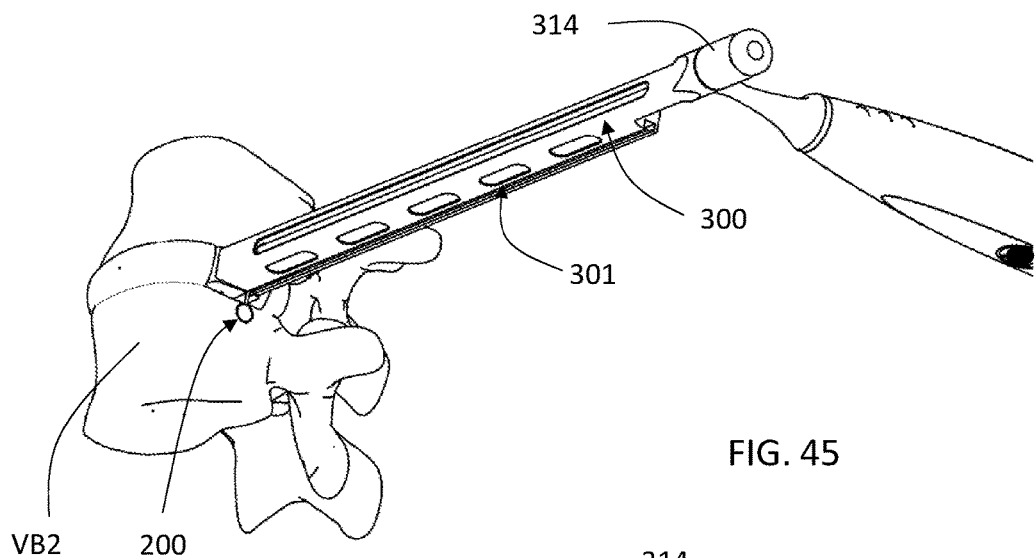
FIG. 45 is a partial bottom perspective view illustrating one step of a method of inserting a spacer and stabilizer whereby a stabilizer implant portion is implanted in a bored hole in a vertebrae.

The selected stabilizer 200 is now attached to a stabilizer inserter 600 by advancing the inserter's prong 603 of inserter insertion tip 602 into the central bore 231 of stabilizer 200 and intermeshing threads 604 with stabilizer threads 232. The base nose 211 at the leading end of stabilizer 200 is then inserted into channel 302 or 303 of inserter tool 300 (FIG. 44) and stabilizer 200 is advanced into the bore created in the vertebrae until stabilizer 200 either buts stabilizer stop 176 or tab 250 springs into undercut region 125. During this process, a sharpened lead edge of a stabilizer cuts through bone until fully seated. The stabilizer inserter 600 is unthreaded from stabilizer 200 and removed (FIG. 45).

Figure 2:
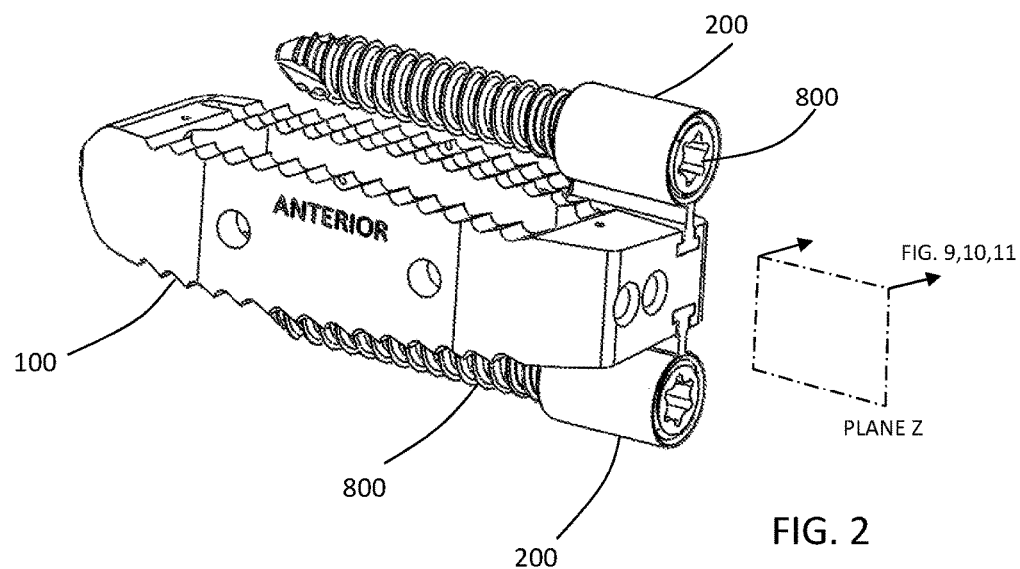
FIG. 2 is a top perspective view of a preferred embodiment of a bone stabilization implant assembly.
Figure 3:
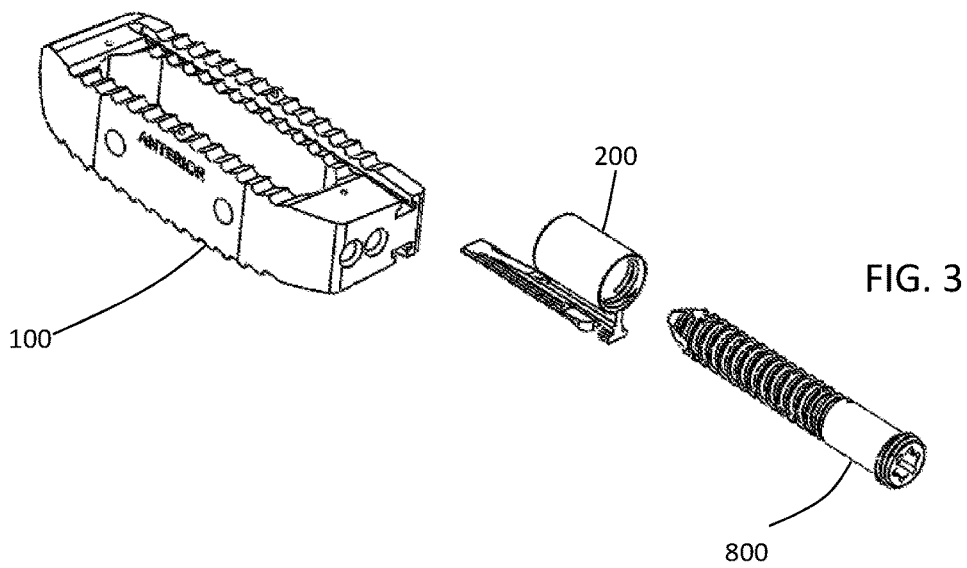
FIG. 3 is an exploded view of the implant assembly illustrated in FIG. 2.
Figure 46:
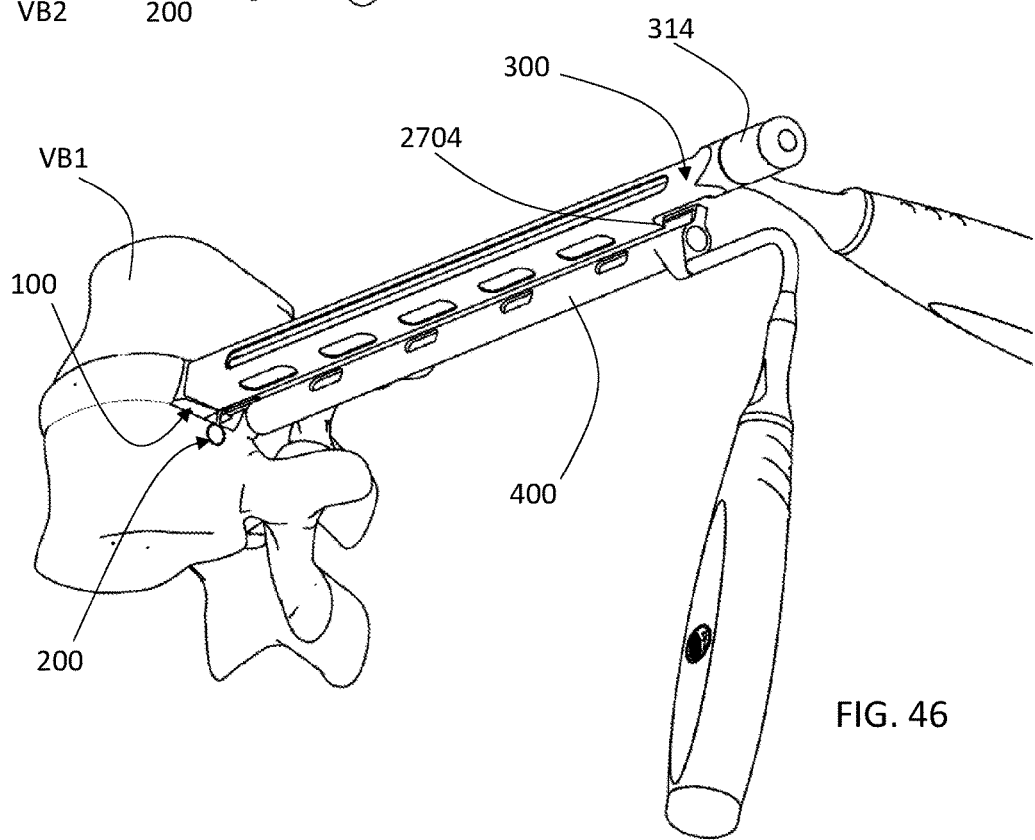
FIG. 46 is a partial bottom perspective view illustrating one step of a method of inserting a spacer and stabilizer whereby a drill guide is coupled with a spacer inserter for future advancement of a stabilizer anchor into a stabilizer implant portion and into a bone.
Figure 47:
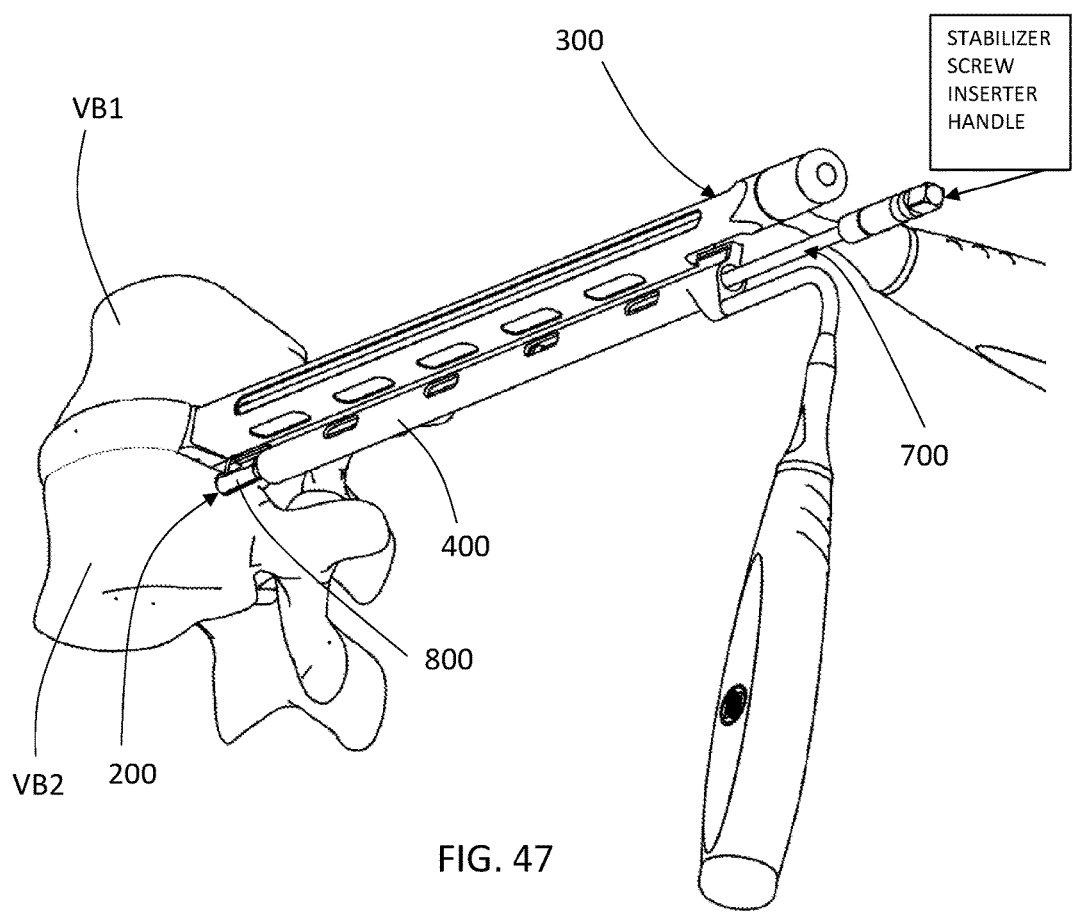
FIG. 47 is a partial bottom perspective view illustrating one step of a method of inserting a spacer and stabilizer whereby a stabilizer anchor is being advanced into a bone.

Drill guide 400 is reinserted into the longitudinal guide 301 and fully advanced (FIG. 46). A threaded stabilizer anchor 800 screw is attached to the stabilizer screw driver 700 and advanced down drill guide 400 and threaded into the pre-drilled bone (FIG. 47). Advancement of anchor 800 continues until threads 825 at head of anchor 800 are fully intermeshed and seated with stabilizer threads 232 such that stabilizer proximal face 221 is generally flush with proximal end of anchor 800 representing a locked state for the stabilizer 200 as illustrated in FIG. 2. At this point the implant has transitioned from a preassembly state to an operative state and from a first state to a locked state.

The stabilizer screw driver 700 and drill guide 400 may now be removed and the procedure repeated on the opposing side until spacer 100 and stabilizers 200 are fully secured thereby achieving an operative relationship between the spacer, stabilizer, and stabilizer anchor.

Where there are cooperating components on separate elements, it is contemplated that the described placement of these components could be reversed. For example, the tabs/barbs 250, shown on the stabilizers 200, could be placed on the spacer/cage 100 with the complementary undercut regions 125 provided on the stabilizer 200. Different combinations and numbers of these paired components can also be utilized.

It is contemplated that structures features from all different embodiments are combinable in different combinations. The foregoing disclosure of specific embodiments is intended to be illustrative of the broad concepts comprehended by the invention.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. An apparatus for stabilization of bones comprising:
   a spacer implant portion;
   said spacer implant portion comprising a body;
   said body having a height sized to fit within a portion of an intervertebral disc space; said body comprising opposed first and second surface portions for spacing adjacent vertebral bodies;
   a pair of opposed channels extending into said opposed first and second surface portions;
   one or more stabilizer implant portions for extending between said spacer implant portion and an intervertebral body;
   said stabilizer implant portion comprising a base wall captured within one of said opposed channels of said body of said spacer implant portion;
   said stabilizer implant portion comprising a cylindrical wall;
   said cylindrical wall comprising a central bore sized for holding a bone screw therein;
   said cylindrical wall spaced from said base wall;
   a web wall extending between said cylindrical wall and said base wall;
   said cylindrical wall comprising a leading end;
   said web wall comprising a sharp leading edge;
   said sharp leading edge of said web wall generally aligned with said leading end of said cylindrical wall;
   said web wall extending to a proximal end of said cylindrical wall;
   said stabilizer implant portion comprising a proximal face on said web wall generally aligned with a proximal end of said spacer implant portion in an operative relationship;
   a stabilizer bone screw separable from said stabilizer cylindrical wall and operable to secure said stabilizer implant portion and said spacer implant portion at a predetermined position with an intervertebral space;
   said stabilizer bone screw at least partially seated within said central bore;
   said stabilizer bone screw comprising a drive head;
   said drive head housed within said central bore of said cylindrical wall in a locked state;
   said drive head sized to advance against said stabilizer implant portion;
   said stabilizer bone screw comprising bone screw threads operable to thread into bone thereby securing said stabilizer implant portion, said spacer implant portion, and said stabilizer bone screw in a predetermined position within an intervertebral space; and
   said bone screw threads passable through said central bore of said cylindrical wall for threading said stabilizer bone screw into bone in a locked state.

2. The apparatus for stabilization of bone of claim 1, wherein said drive head of said stabilizer bone screw comprises screw threads for threaded engagement with threads at a proximal end of a bore surface defining a central bore of said cylindrical wall of said stabilizer implant portion.

3. The apparatus for stabilization of bone of claim 1, wherein said pair of opposed channels extending into said opposed first and second surface portions are generally in the form of T shaped slots.

4. The apparatus for stabilization of bone of claim 3, wherein said base wall and said web wall generally form a T shape sized for fit into said T shaped slots.

5. The apparatus for stabilization of bone of claim 1, wherein said web wall comprises a sharp leading edge for cutting through bone during insertion.

6. The apparatus for stabilization of bone of claim 1, wherein said base wall comprises a barb for preventing unintended back out of said stabilizer implant portion from said spacer implant portion.

7. The apparatus for stabilization of bone of claim 6, wherein said spacer implant portion comprises an undercut region in said channel portion for seating of said barb.

8. The apparatus for stabilization of bone of claim 1, wherein said base wall comprises a stabilizer nose position distally of a leading end of said central bore.

9. The apparatus for stabilization of bone of claim 1, wherein said spacer implant portion, said one or more stabilizer implant portions, and one or more stabilizer bone screw portions are zero profile whereby in an operative configuration no portions of these components protrude from a space between adjacent bone portions.

10. The apparatus for stabilization of bone of claim 1, wherein an operative configuration, a bone stabilization implant assembly comprises one spacer implant portion, two stabilizer implant portions, and two stabilizer bone screw portions.

11. An apparatus for stabilization of bones comprising:
a spacer implant portion;
said spacer implant portion comprising a body;
said body having a height sized to fit within a portion of an intervertebral disc space;
said body comprising opposed first and second surface portions for spacing adjacent vertebral bodies;
a pair of opposed channels extending into said opposed first and second surface portions;
one or more stabilizer implant portions for extending between said spacer implant portion and an intervertebral body;
said stabilizer implant portion comprising a base wall captured within one of said opposed channels of said body of said spacer implant portion in an operative configuration;
said stabilizer implant portion comprising a locking sleeve;
said locking sleeve comprising a central bore;
said locking sleeve spaced from said base wall;
a web wall extending between said locking sleeve and said base wall;
said web wall having a width smaller than said base wall and said locking sleeve;
said locking sleeve comprising a leading end;
said web wall comprising a sharp leading edge;
said sharp leading edge of said web wall generally aligned with said leading end of said locking sleeve;
said web wall extending to a proximal end of said locking sleeve;
a stabilizer bone screw separable from said stabilizer cylindrical wall and operable to secure said stabilizer implant portion and said spacer implant portion at a predetermined position within an intervertebral space;
said locking sleeve sized for holding said stabilizer bone screw therein;
said stabilizer bone screw at least partially seated within said central bore;
said stabilizer bone screw comprising a drive head;
said drive head housed within said central bore of said cylindrical wall in a locked state;
and said stabilizer bone screw comprising bone screw threads operable to thread into bone thereby securing said stabilizer implant portion, said spacer implant portion, and said stabilizer bone screw in a predetermined position within an intervertebral space; and said bone screw threads passable through said central bore of said cylindrical wall for threading into bone in a locked state.

12. The apparatus for stabilization of bone of claim 11, wherein said stabilizer bone screw comprises a drive head with a drive pocket and said drive head is sized to advance against said stabilizer implant portion.

13. The apparatus for stabilization of bone of claim 11, wherein a web wall of two opposing stabilizer implant portions coupled with a spacer implant portion are generally aligned in a single plane in an operative configuration.

14. The apparatus for stabilization of bone of claim 11, wherein said base wall and said web wall generally form a T shape sized for fit into said T shaped slots.

15. The apparatus for stabilization of bone of claim 11, wherein said web wall is 1mm or less thick.

16. The apparatus for stabilization of bone of claim 11, wherein said base wall comprises a barb for preventing unintended back out of said stabilizer implant portion from said spacer implant portion.

17. The apparatus for stabilization of bone of claim 16, wherein said spacer implant portion comprises an undercut region in said channel portion for seating of said barb.

18. The apparatus for stabilization of bone of claim 11, wherein said base wall comprises a stabilizer nose positioned distally of a leading end of said central bore.

19. The apparatus for stabilization of bone of claim 11, wherein said spacer implant portion, said one or more stabilizer implant portions, and one or more stabilizer bone screw portions are zero profile whereby in an operative configuration no portion of these components protrude from a space between adjacent bone portions.

20. The apparatus for stabilization of bone of claim 11, wherein in an operative configuration, a bone stabilization implant assembly comprises one spacer implant portion, two stabilizer implant portions, and two stabilizer bone screw portions.

21. The apparatus for stabilization of bone of claim 11, whereas said spacer implant portion further comprises a nose portion having a lead-in taper.

* * * * *